(12) United States Patent
Kiefer et al.

(10) Patent No.: US 6,903,195 B1
(45) Date of Patent: Jun. 7, 2005

(54) METHODS AND COMPOSITIONS FOR DETECTING CDN APOPTOSIS-MODULATING PROTEINS

(75) Inventors: Michael C. Kiefer, Clayton, CA (US); Philip J. Barr, Berkeley, CA (US)

(73) Assignee: Tanox, Inc., Houston, TX (US)

( * ) Notice: Subject to any disclaimer, the term of this patent is extended or adjusted under 35 U.S.C. 154(b) by 21 days.

(21) Appl. No.: 09/633,200

(22) Filed: Aug. 7, 2000

Related U.S. Application Data

(60) Division of application No. 08/320,157, filed on Oct. 7, 1994, now abandoned, which is a continuation-in-part of application No. 08/160,067, filed on Nov. 30, 1993, now abandoned.

(51) Int. Cl.[7] .................. C07K 16/00; G01N 33/53; G01N 33/567

(52) U.S. Cl. ................ 530/387.1; 530/388.1; 530/388.15; 530/388.8; 530/389.1; 530/389.7; 435/7.1; 435/7.21; 435/7.24

(58) Field of Search .............. 424/130.1, 139.1, 424/141.1, 142.1, 143.1, 152.1, 155.1; 530/387.1, 387.7, 388.1, 388.15, 388.8, 389.1, 389.7; 435/7.1

(56) References Cited

U.S. PATENT DOCUMENTS 5,672,686 A * 9/1997 Chittengen ............... 530/387.9

FOREIGN PATENT DOCUMENTS

WO    WO 96/33416    10/1996

OTHER PUBLICATIONS

Walter, Journal of Immunological Methods, vol. 88, pp. 149–161, 1986.*
Cruse and Lewis, Illustrated Dictionary of Immunology, 1994, p. 241.*
Alignments, from 5,672,686.*
Bowie et al., *Science*, 247:1306–1310 (1990).
Brown, "News Media, Researches 'Oversold' Gene Therapy, Advisory Panel Says," *The Washington Post* (1995).
Buckel, *Trends Pharm. Sci.*, 17:450–456 (1996).
Callard et al., The Cytokine FactBook, Academic Press, London, p. 31 (1994).
Cazals–Hatem et al., *Biochimica et Biophysica Acta*, 1132:109–113 (1992).
Coghlan, *Focus*, 148:14–15 (1995).
Dorin et al., *Gene Ther.*, 3:797–801 (1996).
Dzau et al., *Proc. Natl. Acad. Sci. USA*, 93:11421–11425 (1996).
Grossman et al., *Nat. Genet.*, 6:323 –324 (1994).
Keating et al., Bone Marrow Purging and Processing, 333:491–498 (1990).
Marshall, *Science*, 269:1050–1055 (1995).
Ngo et al., The Protein Folding Problem and Tertiary Structure Prediction, Merz et al., eds., Birkhauser, Boston, pp. 491–495 (1994).
Norrby et al., *APMIS*, 105:417–437 (1997).
Orkin et al., Report and Recommendations of the Panel to Assess the NIH Investment in Research on Gene Therapy (1995).

* cited by examiner

*Primary Examiner*—Susan Ungar
(74) *Attorney, Agent, or Firm*—Sheridan Ross P.C.

(57) ABSTRACT

The present invention provides a novel family of apoptosis-modulating proteins. Nucleotide and amino acid residue sequences and methods of use thereof are also provided.

4 Claims, 29 Drawing Sheets bcl Consensus PCR Primers

```
                                 Ile
    EcoRI AspTrpGlyArgValValAla
    5- AGATCTGAATTCAACTTGGGGGIC(A)GIA(G)TXGTXGC -3'  BCLX 1-32

AspTrpGlyGlyGlnGluAsnAspGlnIleTrp
          AGGGTIGGIGGXACXAGA(G)ACA(T)(C)TAGGT
    5' - AGATCT'AAGCTTGTCCCAICCICCXTGXTCC(T)TGA(G)ATCCA -3'  bclX 2-39
```

```
              10              20              30
               *               *               *
GAG GAT CTA CAG GGG ACA AGT AAA GGC TAC ATC CAG
CTC CTA GAT GTC CCC TGT TCA TTT CCG ATG TAG GTC

>Aha2
       40              50    |        60              70
        *               *               *               *
ATG CCG GGA ATG CAC TGA CGC CCA TTC CTG GAA ACT
TAC GGC CCT TAC GTG ACT GCG GGT AAG GAC CTT TGA 80              90             100
               *               *               *
GGG CTC CCA CTC AGC CCC TGG GAG CAG CAG CCG CCA
CCC GAG GGT GAG TCG GGG ACC CTC GTC GTC GGC GGT 110             120             130             140
               *               *               *               *
GCC CCT CGG ACC TCC ATC TCC ACC TGC CTG AGC CAC
CGG GGA GCC TGG AGG TAG AGG TGG GAC GAC TCG GTG

>SmaI          >BamH1
    |   150       |   160             170             180
        *               *               *               *
CCG GGT TGG GCC AGG ATC CCG GCA GGC TGA TCC CGT
GGC CCA ACC CGG TCC TAG GGC CGT CCG ACT AGG GCA 190             200             210
               *               *               *
CCT CCA CTG AGA CCT GAA AA ATG GCT TCG GGG CAA GGC
GGA GGT GAC TCT GGA CTT TT TAC CGA AGC CCC GTT CCG
                                M   A   S   G   Q   G 220             230             240             250
               *               *               *               *
CCA GGT CCT CCC AGG CAG GAG TGC GGA GAG CCT GCC
GGT CCA GGA GGG TCC GTC CTC ACG CCT CTC GGA CGG
 P   G   P   P   R   Q   E   C   G   E   P   A
```

Fig. 3B

```
         260                    270                    280                    290
          *                      *                      *                      *
CTG CCC TCT GCT TCT GAG GAG CAG GTA GCC CAG GAC
GAC GGG AGA CGA AGA CTC CTC GTC CAT CGG GTC CTG
 L   P   S   A   S   E   E   Q   V   A   Q   D 300                    310                    320
                 *                      *                      *
ACA GAG GAG GTT TTC CGC AGC TAC GTT TTT TAC CGC
TGT CTC CTC CAA AAG GCG TCG ATG CAA AAA ATG GCG
 T   E   E   V   F   R   S   Y   V   F   Y   R 330                    340                    350                    360
          *                      *                      *                      *
CAT CAG CAG GAA CAG GAG GCT GAA GGG GTG GCT GCC
GTA GTC GTC CTT GTC CTC CGA CTT CCC CAC CGA CGG
 H   Q   Q   E   Q   E   A   E   G   V   A   A 370                    380                    390
                 *                      *                      *
CCT GCC GAC CCA GAG ATG GTC ACC TTA CCT CTG CAA
GGA CGG CTG GGT CTC TAC CAG TGG AAT GGA GAC GTT
 P   A   D   P   E   M   V   T   L   P   L   Q

>NcoI
                         |
         400           410                    420                    430
          *             *                      *                      *
                         |
CCT AGC AGC ACC ATG GGG CAG GTG GGA CGG CAG CTC
GGA TCG TCG TGG TAC CCC GTC CAC CCT GCC GTC GAG
 P   S   S   T   M   G   Q   V   G   R   Q   L 440                    450                    460                    470
          *                      *                      *                      *
GCC ATC ATC GGG GAC GAC ATC AAC CGA CGC TAT GAC
CGG TAG TAG CCC CTG CTG TAG TTG GCT GCG ATA CTG
 A   I   I   G   D   D   I   N   R   R   Y   D
```

Fig. 3C

```
                                                      >PstI
            480              490              500      |
             *                *                *
     TCA GAG TTC CAG ACC ATG TTG CAG CAC CTG CAG CCC
     AGT CTC AAG GTC TGG TAC AAC GTC GTG GAC GTC GGG
      S   E   F   Q   T   M   L   Q   H   L   Q   P 510              520              530              540
             *                *                *                *
     ACG GCA GAG AAT GCC TAT GAG TAC TTC ACC AAG ATT
     TGC CGT CTC TTA CGG ATA CTC ATG AAG TGG TTC TAA
      T   A   E   N   A   Y   E   Y   F   T   K   I 550              560              570
             *                *                *
     GCC ACC AGC CTG TTT GAG AGT GGC ATC AAT TGG GGC
     CGG TGG TCG GAC AAA CTC TCA CCG TAG TTA ACC CCG
      A   T   S   L   F   E   S   G   I   N   W   G 580              590              600              610
             *                *                *                *
     CGT GTG GTG GCT CTT CTG GGC TTC GGC TAC CGT CTG
     GCA CAC CAC CGA GAA GAC CCG AAG CCG ATG GCA GAC
      R   V   V   A   L   L   G   F   G   Y   R   L 620              630              640              650
             *                *                *                *
     GCC CTA CAC GTC TAC CAG CAT GGC CTG ACT GGC TTC
     CGG GAT GTG CAG ATG GTC GTA CCG GAC TGA CCG AAG
      A   L   H   V   Y   Q   H   G   L   T   G   F

>SalI
            660              670      |       680
             *                *                *
     CTA GGC CAG GTG ACC CGC TTC GTG GTC GAC TTC ATG
     GAT CCG GTC CAC TGG GCG AAG CAC CAG CTG AAG TAC
      L   G   Q   V   T   R   F   V   V   D   F   M 690              700              710              720
             *                *                *                *
     CTG CAT CAC TGC ATT GCC CGG TGG ATT GCA CAG AGG
     GAC GTA GTG ACG TAA CGG GCC ACC TAA CGT GTC TCC
      L   H   H   C   I   A   R   W   I   A   Q   R
```

Fig. 3D

```
            730                 740                 750
             *                   *                   *
GGT GGC TGG GTG GCA GCC CTG AAC TTG GGC AAT GGT
CCA CCG ACC CAC CGT CGG GAC TTG AAC CCG TTA CCA
 G   G   W   V   A   A   L   N   L   G   N   G 760                 770                 780                 790
      *                   *                   *                   *
CCC ATC CTG AAC GTG CTG GTG GTT CTG GGT GTG GTT
GGG TAG GAC TTG CAC GAC CAC CAA GAC CCA CAC CAA
 P   I   L   N   V   L   V   V   L   G   V   V 800                 810                 820                 830
          *                   *                   *                   *
CTG TTG GGC CAG TTT GTG GTA CGA AGA TTC TTC AAA
GAC AAC CCG GTC AAA CAC CAT GCT TCT AAG AAG TTT
 L   L   G   Q   F   V   V   R   R   F   F   K 840                 850                 860
              *                   *                   *
TCA TGA C TCC CAA GGG TGC CCT TTG GGT CCC GGT TCA
AGT ACT G AGG GTT CCC ACG GGA AAC CCA GGG CCA AGT
 S   *

>Af12
     870                 880  |          890                 900
      *                   *   |           *                   *
GAC CCC TGC CTG GAC TTA AGC GAA GTC TTT GCC TTC
CTG GGG ACG GAC CTG AAT TCG CTT CAG AAA CGG AAG 910                 920                 930
              *                   *                   *
TCT GTT CCC TTG CAG GGT CCC CCC TCA AGA GTA CAG
AGA CAA GGG AAC GTC CCA GGG GGG AGT TCT CAT GTC

>Hind3
   |
  940              950                 960                 970
   *|               *                   *                   *
AAG CTT TAG CAA GTG TGC ACT CCA GCT TCG GAG GCC
TTC GAA ATC GTT CAC ACG TGA GGT CGA AGC CTC CGG
```

Fig. 3E

```
                                              >Pst1
                                                |
      980              990             1000             1010
       *                *                *                *
CTG CGT GGG GGC CAG TCA GGC TGC AGA GGC ACC TCA
GAC GCA CCC CCG GTC AGT CCG ACG TCT CCG TGG AGT

Apa1
             1020             1030            1040      |
              *                *                *
ACA TTG CAT GGT GCT AGT GCC CTC TCT CTG GGC CCA
TGT AAC GTA CCA CGA TCA CGG GAG AGA GAC CCG GGT 1050            1060             1070            1080
       *                *                *                *
GGG CTG TGG CCG TCT CCT CCC TCA GCT CTC TGG GAC
CCC GAC ACC GGC AGA GGA GGG AGT CGA GAG ACC CTG 1090             1100            1110
              *                *                *
CTC CTT AGC CCT GTC TGC TAG GCG CTG GGG AGA CTG
GAG GAA TCG GGA CAG ACG ATC CGC GAC CCC TCT GAC 1120            1130             1140            1150
       *                *                *                *
ATA ACT TGG GGA GGC AAG AGA CTG GGA GCC ACT TCT
TAT TGA ACC CCT CCG TTC TCT GAC CCT CGG TGA AGA 1160            1170             1180            1190
       *                *                *                *
CCC CAG AAA GTG TTT AAC GGT TTT AGC TTT TTA TAA
GGG GTC TTT CAC AAA TTG CCA AAA TCG AAA AAT ATT 1200             1210            1220
              *                *                *
TAC CCT TGT GAG AGC CCA TTC CCA CCA TTC TAC CTG
ATG GGA ACA CTC TCG GGT AAG GGT GGT AAG ATG GAC

Aha2
     1230    |       1240             1250            1260
       *                *                *                *
AGG CCA GGA CGT CTG GGG TGT GGG GAT TGG TGG GTC
TCC GGT CCT GCA GAC CCC ACA CCC CTA ACC ACC CAG
```

Fig. 3F

```
         1270              1280              1290
           *                 *                 *
TAT GTT CCC CAG GAT TCA GCT ATT CTG GAA GAT CAG
ATA CAA GGG GTC CTA AGT CGA TAA GAC CTT CTA GTC 1300          1310          1320          1330
    *             *             *             *
CAC CCT AAG AGA TGG GAC TAG GAC CTG AGC CTG GTC
GTG GGA TTC TCT ACC CTG ATC CTG GAC TCG GAC CAG 1340          1350         1360         1370
           *             *            *            *
CTG GCC GTC CCT AAG CAT GTG TCC CAG GAG CAG GAC
GAC CGG CAG GGA TTC GTA CAC AGG GTC CTC GTC CTG
              1380          1390         1400
                *             *            *
CTA CTA GGA GAG GGG GGC CAA GGT CCT GCT CAA CTC
GAT GAT CCT CTC CCC CCG GTT CCA GGA CGA GTT GAG 1410         1420          1430         1440
    *            *             *            *
TAC CCC TGC TCC CAT TCC TCC CTC CGG CCA TAC TGC
ATG GGG ACG AGG GTA AGG AGG GAG GCC GGT ATG ACG 1450            1460            1470
           *               *               *
CTT TGC AGT TGG ACT CTC AGG GAT TCT GGG CTT GGG
GAA ACG TCA ACC TGA GAG TCC CTA AGA CCC GAA CCC 1480          1490          1500          1510
    *             *             *             *
GTG TGG GGT GGG GTG GAG TCG CAG ACC AGA GCT GTC
CAC ACC CCA CCC CAC CTC AGC GTC TGG TCT CGA CAG 1520          1530          1540          1550
    *             *             *             *
TGA ACT CAC GTG TCA GAA GCC TCC AAG CCT GCC TCC
ACT TGA GTG CAC AGT CTT CGG AGG TTC GGA CGG AGG 1560            1570            1580
           *               *               *
CAA GGT CCT CTC AGT TCT CTC CCT TCC TCT CTC CTT
GTT CCA GGA GAG TCA AGA GAG GGA AGG AGA GAG GAA
```

Fig. 3G

```
        1590              1600              1610              1620
         *                 *                 *                 *
ATA GAC ACT TGC TCC CAA CCC ATT CAC TAC AGG TGA
TAT CTG TGA ACG AGG GTT GGG TAA GTG ATG TCC ACT 1630              1640              1650
             *                 *                 *
AGG CTC TCA CCC ATC CCT GGG GGC CTT GGG TGA GTG
TCC GAG AGT GGG TAG GGA CCC CCG GAA CCC ACT CAC 1660         1670              1680              1690
      *            *                 *                 *
GCC TGC TAA GGC TCC TCC TTG CCC AGA CTA CAG GGC
CGG ACG ATT CCG AGG AGG AAC GGG TCT GAT GTC CCG 1700              1710              1720              1730
          *                 *                 *                 *
TTA GGA CTT GGT TTG TTA TAT CAG GGA AAA GGA GTA
AAT CCT GAA CCA AAC AAT ATA GTC CCT TTT CCT CAT 1740              1750              1760
             *                 *                 *
GGG AGT TCA TCT GGA GGG TTC TAA GTG GGA GAA GGA
CCC TCA AGT AGA CCT CCC AAG ATT CAC CCT CTT CCT

>BamH1
      1770              1780              1790     |    1800
       *                 *                 *       |     *
CTA TCA ACA CCA CTA GGA ATC CCA GAG GTG GAT CCT
GAT AGT TGT GGT GAT CCT TAG GGT CTC CAC CTA GGA 1810              1820              1830
             *                 *                 *
CCC TCA TGG CTC TGG CAC AGT GTA ATC CAG GGG TGT
GGG AGT ACC GAG ACC GTG TCA CAT TAG GTC CCC ACA 1840         1850              1860              1870
        *            *                 *                 *
AGA TGG GGG AAC TGT GAA TAC TTG AAC TCT GTT CCC
TCT ACC CCC TTG ACA CTT ATG AAC TTG AGA CAA GGG
```

Fig. 3H

```
          1880                1890                1900                1910
            *                   *                   *                   *
      CCA CCC TCC ATG CTC CTC ACC TGT CTA GGT CTC CTC
      GGT GGG AGG TAC GAG GAG TGG ACA GAT CCA GAG GAG 1920                1930                1940
          *                   *                   *                   *
      AGG GTG GGG GGT GAC AGT GCC TTC TCT ATT GGC ACA
      TCC CAC CCC CCA CTG TCA CGG AAG AGA TAA CCG TGT 1950                1960                1970                1980
            *                   *                   *                   *
      GCC TAG GGT CTT GGG GGT CAG GGG GGA GAA GTT CTT
      CGG ATC CCA GAA CCC CCA GTC CCC CCT CTT CAA GAA 1990                2000                2010
                *                   *                   *
      GAT TCA GCC AAA TGC AGG GAG GGG AGG CAG ATG GAG
      CTA AGT CGG TTT ACG TCC CTC CCC TCC GTC TAC CTC
      2020            2030                2040                2050
        *               *                   *                   *
      CCC ATA GGC CAC CCC CTA TCC TCT GAG TGT TTG GAA
      GGG TAT CCG GTG GGG GAT AGG AGA CTC ACA AAC CTT 2060                2070                2080                2090
              *                   *                   *                   *
      ATA AAC TGT GCA ATC CCC TCA AAA AAA AAA CGG AGA
      TAT TTG ACA CGT TAG GGG AGT TTT TTT TTT GCC TCT

TCC
      AGG
```

Fig. 5A

```
                 10                  20                  30
                  *                   *                   *
        TTT TAA TAT AAA TTA ATG TGC TCT ATT TAT AGA GAC
        AAA ATT ATA TTT AAT TAC ACG AGA TAA ATA TCT CTG 40                  50                  60                  70
          *                   *                   *                   *
        AAT ACA TGA AAT ATA CTT AAT AAA AAT TCA AAT GTT
        TTA TGT ACT TTA TAT GAA TTA TTT TTA AGT TTA CAA 80                  90                 100
                  *                   *                   *
        ATA GAA CTG AAA AAG ATG AAA AGT AAA AAC AAC CTA
        TAT CTT GAC TTT TTC TAC TTT TCA TTT TTG TTG GAT 110                 120                 130                 140
         *                   *                   *                   *
        TTC CCC AGA GGT AGC CAC TGT CCA TAG TTT CTA TTT
        AAG GGG TCT CCA TCG GTG ACA GGT ATC AAA GAT AAA 150                 160                 170                 180
                 *                   *                   *                   *
        TAG ATT CTT TCC TTT ATA CAA GAT TAT TAT AGC TTC
        ATC TAA GAA AGG AAA TAT GTT CTA ATA ATA TCG AAG 190                 200                 210
                 *                   *                   *
        TAT TTT TTG GTG TAT GAA CTG TAG TCC TAG AGG ATT
        ATA AAA AAC CAC ATA CTT GAC ATC AGG ATC TCC TAA 220                 230                 240                 250
         *                   *                   *                   *
        TTA TTA GTT ATG AGT TCT ATA ACT AAG ATC CAT CAT
        AAT AAT CAA TAC TCA AGA TAT TGA TTC TAG GTA GTA 260                 270                 280
                 *                   *                   *
        CTT AGT TGC TAA GAA CGT AGA TAC TGA GAA CAT CAT
        GAA TCA ACG ATT CTT GCA TCT ATG ACT CTT GTA GTA
```

Fig. 5B

```
        290              300              310              320
         *                *                *                *
TTA AAA AAA CAT TTT TGG CTG GCA CCT CAT GAT CAC
AAT TTT TTT GTA AAA ACC GAC CGT GGA GTA CTA GTG 330              340              350              360
         *                *                *                *
TGG AGT CTC GCG GGT CCC TCA GGC TGC ACA GGG ACA
ACC TCA GAG CGC CCA GGG AGT CCG ACG TGT CCC TGT 370              380              390
             *                *                *
AGT AAA GGC TAC ATC CAG ATG CTG GGA ATG CAC TGA
TCA TTT CCG ATG TAG GTC TAC GAC CCT TAC GTG ACT 400              410              420              430
         *                *                *                *
CGC CCA TTC CTG GAA ACT GGG CTC CCA CTC AGC CCC
GCG GGT AAG GAC CTT TGA CCC GAG GGT GAG TCG GGG 440              450              460
             *                *                *
                                                     > BamHI
        470              480              490      500|
         *                *                *        *  |
CTC CAC CCT GCT GAG CCA CCC GGG TTG GGC CAG GAT
GAG GTG GGA CGA CTC GGT GGG CCC AAC CCG GTC CTA

TGG GAG CAG CAG CCG CCA GCC CCT CGG GAC CTC CAT
ACC CTC GTC GTC GGC GGT CGG GGA GCC CTG GAG GTA 510              520              530              540
         *                *                *                *
CCC GGC AGG CTG ATC CCG TCC TCC ACT GAG ACC TGA
GGG CCG TCC GAC TAG GGC AGG AGG TGA CTC TGG ACT 550              560              570
             *                *                *
AAA ATG GCT TCG GGG CAA GGC CCA GGT CCT CCC AGG
TTT TAC CGA AGC CCC GTT CCG GGT CCA GGA GGG TCC
     M   A   S   G   Q   G   P   G   P   P   R
```

Fig. 5C

```
        580                 590                 600                 610
         *                   *                   *                   *
CAG GAG TGC GGA GAG CCT GCC CTG CCC TCT GCT TCT
GTC CTC ACG CCT CTC GGA CGG GAC GGG AGA CGA AGA
 Q   E   C   G   E   P   A   L   P   S   A   S 620                 630                 640
              *                   *                   *
GAG GAG CAG GTA GCC CAG GAC ACA GAG GAG GTT TTC
CTC CTC GTC CAT CGG GTC CTG TGT CTC CTC CAA AAG
 E   E   Q   V   A   Q   D   T   E   E   V   F 650                 660                 670                 680
  *                   *                   *                   *
CGC AGC TAC GTT TTT TAC CAC CAT CAG CAG GAA CAG
GCG TCG ATG CAA AAA ATG GTG GTA GTC GTC CTT GTC
 R   S   Y   V   F   Y   H   H   Q   Q   E   Q 690                 700                 710                 720
              *                   *                   *                   *
GAG GCT GAA GGG GCG GCT GCC CCT GCC GAC CCA GAG
CTC CGA CTT CCC CGC CGA CGG GGA CGG CTG GGT CTC
 E   A   E   G   A   A   A   P   A   D   P   E

>NcoI
             730                 740                 750   |
              *                   *                   *    |
ATG GTC ACC TTA CCT CTG CAA CCT AGC AGC ACC ATG
TAC CAG TGG AAT GGA GAC GTT GGA TCG TCG TGG TAC
 M   V   T   L   P   L   Q   P   S   S   T   M 760                 770                 780                 790
  *                   *                   *                   *
GGG CAG GTG GGA CGG CAG CTC GCC ATC ATT GGG GAC
CCC GTC CAC CCT GCC GTC GAG CGG TAG TAA CCC CTG
 G   Q   V   G   R   Q   L   A   I   I   G   D
```

Fig. 5D

```
       800                810                820
         *                  *                  *
GAC ATC AAC CGA CGC TAT GAC TCA GAG TTC CAG ACC
CTG TAG TTG GCT GCG ATA CTG AGT CTC AAG GTC TGG
 D   I   N   R   R   Y   D   S   E   F   Q   T

>PstI
       830                840         |       850                860
         *                  *                  *                  *
ATG TTG CAG CAC CTG CAG CCC ACG GCA GAG AAT GCC
TAC AAC GTC GTG GAC GTC GGG TGC CGT CTC TTA CGG
 M   L   Q   H   L   Q   P   T   A   E   N   A 870                880                890                900
         *                  *                  *                  *
TAT GAG TAC TTC ACC AAG ATT GCC TCC AGC CTG TTT
ATA CTC ATG AAG TGG TTC TAA CGG AGG TCG GAC AAA
 Y   E   Y   F   T   K   I   A   S   S   L   F 910                920                930
                *                  *                  *
GAG AGT GGC ATC AAT TGG GGC CGT GTG GTG GCT CTT
CTC TCA CCG TAG TTA ACC CCG GCA CAC CAC CGA GAA
 E   S   G   I   N   W   G   R   V   V   A   L 940                950                960                970
         *                  *                  *                  *
CTG GGC TTC AGC TAC CGT CTG GCC CTA CAC ATC TAC
GAC CCG AAG TCG ATG GCA GAC CGG GAT GTG TAG ATG
 L   G   F   S   Y   R   L   A   L   H   I   Y 980                990                1000
                *                  *                  *
CAG CGT GGC CTG ACT GGC TTC CTG GGC CAG GTG ACC
GTC GCA CCG GAC TGA CCG AAG GAC CCG GTC CAC TGG
 Q   R   G   L   T   G   F   L   G   Q   V   T
```

Fig. 5E

```
       1010                1020                1030                1040
         *                   *                   *                   *
CGC TTT GTG GTG GAC TTC ATG CTG CAT CAC TGC ATT
GCG AAA CAC CAC CTG AAG TAC GAC GTA GTG ACG TAA
 R   F   V   V   D   F   M   L   H   H   C   I 1050                1060                1070                1080
         *                   *                   *                   *
GCC CGG TGG ATT GCA CAG AGG GGT GGC TGG GTG GCA
CGG GCC ACC TAA CGT GTC TCC CCA CCG ACC CAC CGT
 A   R   W   I   A   Q   R   G   G   W   V   A 1090                1100                1110
                  *                   *                   *
GCC CTG AAC TTG GGC AAT GGT CCC ATC CTG AAC GTG
CGG GAC TTG AAC CCG TTA CCA GGG TAG GAC TTG CAC
 A   L   N   L   G   N   G   P   I   L   N   V 1120                1130                1140                1150
         *                   *                   *                   *
CTG GTG GTT CTG GGT GTG GTT CTG TTG GGC CAG TTT
GAC CAC CAA GAC CCA CAC CAA GAC AAC CCG GTC AAA
 L   V   V   L   G   V   V   L   L   G   Q   F 1160                1170                1180
                  *                   *                   *
GTG GTA CGA AGA TTC TTC AAA TCA TGA CTC CCA AGG
CAC CAT GCT TCT AAG AAG TTT AGT ACT GAG GGT TCC
 V   V   R   R   F   F   K   S   *

1190                1200                1210                1220
         *                   *                   *                   *
GTG CCT TTG GGG TCC CAG TTC AGA CCC CTG CCT GGA
CAC GGA AAC CCC AGG GTC AAG TCT GGG GAC GGA CCT 1230                1240                1250                1260
         *                   *                   *                   *
CTT AAG CGA AGT CTT TGC CTT CTC TGC TCC TTG CAG
GAA TTC GCT TCA GAA ACG GAA GAG ACG AGG AAC GTC
```

Fig. 5F

```
                                    >Hind3
           1270             1280      |
            *                *
GGT CCC CCC TCA AGA GTA CAG AAG CTT
CCA GGG GGG AGT TCT CAT GTC TTC GAA
```

```
cdn1                                                         masgqgppqrqecgepalpsaseeqvaqdteevfrsyvfyrhqqeqeaegvaapadpemvt
cdn2                                                         masgqgppgrqecgepalpsaseeqvaqdteevfrsyvfyHhqqeqeaegAaapadpemvt
bcl2                                            mahagrtgyDNREIVMKYIHYKLSQRGYEWdagdvgaappgaapapgifssqpghtphtaasrdpvartsplqtpaapgaa
bax                                                                              mdgsgeqprgggptsseqimktgallllqgfiqdragrmggeap
bcl-x                                                   msqSNRELVVDFLSYKLSQKGYSWksqfsdveenrteapegtesemetpsaingnpswhladspavngatghsssl
mcl-1                                 ...(+123 aa)eldgsyepeplgkrpavlpllelvgesGnntstdgslpstpppaeeeedelyrqsleiisrylreqatgakdtk
A1                                                                                                        maeselmhihslaehylqyvlq
bhrf                                                                                          maystreillalcirdsrvhgngtlhpvlelaar
LMW5-HL                                                                                                     megeeliyhniineilvgy
ced9     mtrctadnsltnpayrrrtmatgemkeflgikgteptdfginsdaqdlpspsrqastrrmsigesidgkindweeprlDIEGFVVDYFTHRIRQNGMEWfgapg cdn1     lplqpsstmgQVGRQLAIIGDDINRRYDSEFQTMLQHLQPTAENAYEYFTKIATSLFESGI-NWGRVVALLGFGYRLALHVYQHGLTGFLGQVTRFVVDFMLHH
cdn2     lplqpsstmgQVGRQLAIIGDDINRRYDSEFQTMLQHLQPTAENAYEYFTKIASSLFESGI-NWGRVVALLGFGYRLALHIYQRGLTGFLGQVTRFVVDFMLHH
bcl2     agpalspvppVVHLTLRQAGDDFSRRYRRDFAEMSRQLHLtpftargRFATVVEELFRDGV-NWGRIVAFFEFGGVMCVESVNREMSPLVDNIALWMTEY-LNR
bax      elaldpvpqdastkklseclkrigdeldsnmelqrmiaavdtdsprevFFRVAADMFSDGNFNWGRVALFYFASKLVLKALCTKVPELIRTIMGWTLDF-LRE
bcl-x    darevipma-AVKQALREAGDEFELRYRRAFSDLTSQLHITPGTAYQSFEQVVNELFRDGV-NWGRIVAFFSFGGALCVESVDKEMQVLVSRIAAWMATY-LND
mcl-1    pmgrsgatsrkalETLRRVGDGVQRNHETVFQGMLRKLDIKNEDDVKSLSRVMIHVFSDGVTNWGRIVTLISFGAFVAKHLKTINQESCIEPLAESITD-VLVR
A1       vpafesapsqacrvlqrvafsvqkeveknlksylddfhvesidtariiFNQYMEKEFEDGIINWGRIVTIFAFGGVLLKKLpqeqialdvcaykqvssfvaefi
bhrf     etplrlspedtvvlryhvlleeiiernsetffetwnrfithtehvdldfnsvfleifhD-LINWGRICGFIVFSARMAKYCKDANn-HLESTVITTAYNF-SEG
LMW5-HL  ikyymndihelspyqqikkiltyydeclnkqvtitfsltnaqeiktQFTGVVTELFKrgdpslgralawmawcmhacrtlccnqstpyyvvdlsvrgmleaM-
ced9     lpcgvqpehemmrvmgtifekkhaenfetfceqllavprisflyqdvvrtvgnaqtdqcpMSYGRLIGLISFGGFVAAKMmesvelggqvrnlfvytslfIKT cdn1     CIAR--WIA-QR-GGWVAALNLGngpilnvlvvlgvvllgqfvvrffks
cdn2     CIAR--WIA-QR-GGWVAALNLGngpilnvlvvlgvvllgqfvvrffks                SEQUENCE IDENTITY:
bcl2     HLHT--WI--QDNGGWDAFVELYgpsmrplfdfswlslktllslalvgacitlgaylghk
bax      RLLG--WI--QDQGGWDGLLSYFgtptwqtvtifvagvltasltiwkkmg                     cdn1/cdn2 = 97%
bcl-x    HLEP--WI--QENGGWDTFVELYgnnaaaesrkgqerfnrwfltgmtvagvyllgslfsrk
mcl-1    TKRD--WLVKQ--RGWDGFVEFFhvedleggirnvllafagvagvaglaylir
A1       MNNTGEWI-RQ--NGGWEdgfikkfepksgwltflqmtggiwemifllk                        FIG. 6
bhrf     -LDG--WIHQQ--GGWStliednipgsrrfswtlflagitlsllvicsylfisrgrh
LMW5-HL  KHNLLPWMISH--GGQEEFLAFslhsqiysvifnikyflskfcnhhflrscvqllrkcnli
ced9     -RIRNNWKE-H--NRSWDDFMTLgkqmkedyeraeaekvgrrkqnrrwsmigagvtagaigivgvvvcgrmmfslk
```

```
                                                                              80
         *         *         *         *         *         *         *         *
GAATTCTGGT AATTAGTTAA ACAACCTTGA ACAAGTTGTT TCACTTCTCT GAGTCTCAGT TTCTCACTCA AAAATGGTGA
                                                                             160
         *         *         *         *         *         *         *         *
ATAATTTGTA AGACTTCGCT AATAATCTAC GACTCTACAA GAGGCAATAG GGTACTGTGG ACAGAGAGCA GGCTTTGGAA

240
         *         *         *         *         *         *         *         *
ACACACAAGA CTGGGTTTAG ATTCCTGCAC TCCACCCAGT GTGTGACTTG GCCAAGCTTC TTCACTTCTC TAAACCCCCA
                                                                             320
         *         *         *         *         *         *         *         *
TCTGTGTATC TGTACAGGAA TGAATGAATG AGTATGTGCA GCCAAGCTAT GCAAACTCCA GGTTAAAATA TTGCCTTGGG

400
         *         *         *         *         *         *         *         *
TTTTTTAGTA AATTGTTCAA GCCCATGACA TTCTAGCAGA AAAAGCCTAG TGTCTCTTTC TTAAGGTGAT TGTGTCCATG
                                                                             480
         *         *         *         *         *         *         *         *
TGTTTTCCAG GAACTCTATG GGTTTCTCAA CCCAAATTCA CCCTGCCCTT GACCAAATGG CTCACCAGCT TCACGGATGC

560
         *         *         *         *         *         *         *         *
TGCTCTGATG ACACACCCTG CAGTCAGCAT CTGCCCCTGC AGCTAGAATG GATTTCTGAG TGGGCATTAG CTGGGGGATA

640
         *         *         *         *         *         *         *         *
CCACATGGGC ACCAATGTCA CAGATCTTCT GTCACAGTCC ACCCCGAACC ATTGCTTCTC AAATCATAAT CCCTTAGCAG

720
         *         *         *         *         *         *         *         *
GACAGCTAGG TGCAGCACGC ATGACACAAA CACCAGCCCT TGCCTACAAT CTCAGCCACT ATCTTGAGTC TGAGCAACTA
                                                                             800
         *         *         *         *         *         *         *         *
GTCTAGTGGC AGCCGCGCCC TTCCTTTTCA AGAGAGTTCT GGGATCAGAT CCTTTCACAA ACAGATCCCT CCCCACCCTG
                                                                             880
         *         *         *         *         *         *         *         *
CCTGTTGTCC AGGTCTGCAC ACTGAAAAGT AAGACAGCAT TTGCTAAGCC ATATTTCAAA AAGTTTGCTT ATACCTTCAT
```

FIG. 7A

```
                                                                                960
         *          *          *          *          *          *          *     *
CTCAGGACAA CAAGTGCCTG CTTAAGAGCC TTATGTTTGT GTAACTGGTA TTTTTTTTTC CCCTGACCTT CCAAGGCCTA

1040
         *          *          *          *          *          *          *     *
GTCTACTTTC TCCCTCCCTA GCTGAACAAA AGTGAAGTTG AAATAATTTG AACTACCCCT TTTAGTGGGC AGCCCATTTG

1120
         *          *          *          *          *          *          *     *
ATTTTTACCT TAGCCAGAGC CTTAATTTGT CCATGTGAGC ATAGCAGTAC CTTGCAGCAC CTGAGGCACA ATACATTGTT

*          *          *          *          *          *          *     *
TAAAGAGTGA CAGTGCGTCC CATTCCAATA AGAACCACAC TCAGAGCAAA GGTTCCCTCT CCTGTGTGGA GAGTGACCCA

1280
         *          *          *          *          *          *          *     *
TGGTAGAAAA TTTGCAGACT TCGTTACCTC TTCATCAGTT GAAAAATCTA TTTATTCATT TATGCATTTA ATTTTCCCTA

1360
         *          *          *          *          *          *          *     *
TCTAAGCCAG GGATAGTCAA ACATTTTCTG TAAAGGGCCA AGTAGCATGA TAAATATGTT AGGCTCTGCA GGCCACTTAC

1440
         *          *          *          *          *          *          *     *
AGTTTTGTCA TGTATTCTTT TTTTGCTCCC TGTTTGTATT ATTTTGTTTA CAATGCTTTA AAAATGTAAA AAAACAGATG

*          *          *          *          *          *          *     *
ATCACTGGAG TCTCACGGGT CCCTCGGGCC ACACAGGGAC AAGCAAAGGC TACATCCAGA TACCAGAAAT GCACTGACGC

1600
         *          *          *          *          *          *          *     *
CCGTTCCTGG AAGCTGGGCT CCCACTCAGC CCTGGGAGC AGCAGCCTCC AGCCCCTTGG GACCTTCAAC TCCACCCTGC

*          *          *          *          *          *          *     *
TGACCCACGC GGGTTGAGCC AGCATCCCTG GAGGCTGACA CTGTCCTCCA CTGAGACCTG AAAA ATG GCA TCG GGG
                                                                         M   A   S   G>
```

FIG. 7B

```
1680
 *              *                *              *                *              *                *
CAA GGC CCA GGG CCT CCC AGG CAG GAG TGC GGA AAG CCT GCC CTG CCC TCT GCT TCT GAG GAG CAG
 Q   G   P   G   P   P   R   Q   E   C   G   K   P   A   L   P   S   A   S   E   E   Q>

1760
               *                *              *                *              *
GTA GCC CAG GAC ATG GAG GGG TTT TCC GCA GCT ACG TTT TTT ACC ACC ATC AGC AGG AAC AGG AGG
 V   A   Q   D   M   E   G   F   S   A   A   T   F   F   T   T   I   S   R   N   R   R>

1840
 *              *                *         *     *              *                *
CTG AAG GGG CGG CCG CCC CTG CCG ACC CAG AGA TGG TCA CCT TGC CCC TCC AAC CTA GCA GCA CCA
 L   K   G   R   P   P   L   P   T   Q   R   W   S   P   C   P   S   N   L   A   A   P>

1920
 *              *                *              *         *      *                *
TGG GGC AGG TGG GAC GGC AGC TCG CCA TCA CCA GGA CGA CAT CAA CCG GCA CTA TGA CTTCGGAGT
 W   G   R   W   D   G   S   S   P   S   P   G   R   H   Q   P   A   L   *>

2000
   *            *           *            *            *      *            *            *
TCCAGACCAT GCTGCAGCAC CTGCAGCCCA CGGCAGAGAA CGCCTACGAG TACTTCACCA AGATCGCCTC CAGCCTGTTT

2080
   *            *           *            *            *            *      *            *
GAGAGTGGCA TCAACCGGGG CCGTGTGGTG GCTCTCCTGG GCTTCGGCTA CCGTCTGGTC CTACATGTCT ACCAGCACGG

2160
   *            *           *            *            *           *       *            *
CTTGACTGGC TTCCTGGGCC TGGTGACCCG CTTCGTGGTC TTCATGCTGC AACAAGGCAT CGCCCGGTGG ATCTCGCAGA

2240
   *            *           *            *            *            *      *            *
GGGGCGGCTG GGTGGCAGCC CTGGACTTGG GCAATAGTCC CATCCTGAAC GTGCTGGTGG TTGTGGGTGT GGTTCTGCTG

2320
   *            *           *            *            *      *            *            *
GGCCAGTTTG TGGTAAGAAG ATTCTTCAAA TCATGACTCC CAGGGGTGTC CTTTGGGGTC CCAGCTGTGA CCCCTGCCTG

2400
   *            *           *            *            *      *            *            *
GACTTAAGCC AAGTCTTTGC CTTCCCCACT CCCTTGCAGG GGTCACCCTT CAAAAGTACA GAAGCTCTAG CAAGTGTGCA
```

FIG. 7C

```
                *          *          *          *          *     2480 *          *          *
       CCCCCGCTGC GGAGGGCCCC TGCGTGGGGG CCAGTCAGGC TGCGGAGGCA CCTCAACATT GCACGGTGCT AGTGGGCCCT

*          *          *          *          *     2560 *          *          *
       CTCTCTGGGC CCAGGGGCTG TGCCCTCCTC CCTTGGCTCT CTGGGACCTC CTTAGTCTTG TCTGCTAGGC GCTGCAGAGG

*          *          *          *          *     2640 *          *          *
       CTGATAACTT GGGGAAGCAA GAGACTGGGA GCCACTCCTC CCCAGTAAGT GTTTAACGGT TTTAGCTTTT TATAATACCC

*          *          *          *          *     2720 *          *          *
       TTGGGAGAGC CCATTCCCAC CATTCTACCC AAGGCCGGGA TGTCTGGGGT GTGGGGGTTG GTGGGTCGTA ACCTACGTGC

*          *          *          *          *     2800 *          *          *
       CCCAGGATTC AGCTATTCTG GAAGATCAGA GCCTAAGAGC TAGGACTTGA TCCTGGTCCT GGCCGTCCCT AAGCATCATG

*          *          *          *          *     2880 *          *          *
       TGTCCCAGGA GCAGGACTGA CTGGGAGAGG GGACCAAGGT CCTACCCAGC TCTCCCCGTG CCCCCATTCC TCCTCCGGCC

*          *          *          *          *     2960 *          *          *
       ATACTGCCTT TGCAGTTGGA CTCTCAGGGA TTCTGGGCTT GGGGTGTGGG GCGGCGTGGA GTAACAGGCC AGAGCTGTCT

*          *          *          *          *     3040 *          *          *
       GAACTTATGT GTCAGAAGCC TCCAAGCCTG CCTCCCAAGG TCCTCTCAGC TCTCTCCCTT CCTCTCTCCT TATAGATACT

*          *          *          *          *     3120 *          *          *
       TGCTCCCAAC CCATTCACTA CAGGTGAAGG CCCTCACCCA TCCCTGGGGG CCTTGGGTGA GTGATGCGCT AAGGCCCCTC

*          *          *          *          *     3200 *          *          *
       CCCGCCCAGA CTACAGGGCT TGGTTTAGGG CTTGGTTTGT TATTTCAGGG ATAAGGAGTA GGGAGTTCAT CTGGAAGGTT

*          *          *          *          *     3280 *          *          *
       CTAAGTGGGA GAAGGACTAT CAACACCACA GGAATCCCAG AGGTGGGATC CTCCCTCATG GCTCTGGCAC AGTGTAATCC
                *          *          *          *          *     3360 *          *          *
       AGGGGTGGAG ATAGGGAACT GTGAATACCT GAACTCTGTC CCCCGACCCT CCATGCTCCT CACCTTTCTG GGTCTCTCCT
```

FIG. 7D

```
                                                      3440
       *          *          *          *          *    *          *          *
CAGTGTGGGG GTGAGAGTAC CTTCTCTATC GGGCACAGCC TAGGGTGTTG GGGGTGAAGG GGGAGAAGTT CTTGATTCAG
                                                      3520
       *          *          *          *          *    *          *          *
CCAAATGCAG GGAGGGGAGG CAGAAGGAGC CCACAGGCCA CTCCCTATCC TCTGAGTGTT TGGAAATAAA CTGTGCAATC
                                                      3600
       *          *          *          *          *    *          *          *
CCATCAAAAA AAAAAAGGAG AAAAAAATGT AAAAAACATT CTTAGCTGTA AGCTACTTAT AGGGGGATAA AGACAGGACT
                                                      3680
       *          *          *          *          *    *          *          *
GTTAATGGAC ACAAACATAC AGTTAGAGAG AAGAAATAAG TTCTGTCCAG GCACGGTGGC TCACACCTCT AACTCCAGCA
                                                      3760
       *          *          *          *          *    *          *          *
CTTTGGGAGA CCAAAGTGGG AAGATCATTT GAGTCCAGGA GTTCGAGACC AGCCTGGACA ACATAGCAAG ATCTTATCTC
                                                      3840
       *          *          *          *          *    *          *          *
TACAGAAAAT TTAAAAAAAA GAAAAAAACT AGCCGCACAG GTCTGCAGTC CTAGCTACTC GGGAGGCTAA GGTGGGAGAA
                                                      3920
       *          *          *          *          *    *          *          *
TCCTTGAACC CAGGGATTTA GTTTGAGGTT GCAGTGAGCT ATGATTGCAC CACTGCACTC CAGACTGGGT GACTGAGTGA
                                                      4000
       *          *          *          *          *    *          *          *
GACCCTGTCT CAAATATAAA GAAGGAACAA GTTCTAGTTT TCAATAGCGC AATAGGGTGA GTGCAGTTAG CAACAACATA
                                                      4080
       *          *          *          *          *    *          *          *
TTGTGTATTT CAAAATAGCT ACAAGAGAGG ATATGAAGTG TTCCCCCAAA CAAGGAATGA TAACGTTCGA GGTGACAGAT
                                                      4160
       *          *          *          *          *    *          *          *
ACCTTAAATA CCCTGATTTG ATCATTACAC ATTCAATGTA TGTATCAAAA TATTACATGT ACCCCACAAA TTTGTGTAAA
                                                      4240
       *          *          *          *          *    *          *          *
TATTATGTAT CCACTTTTTA AAGTTGGCAG AGCCCAAAAG CACTACTATG GCTTCCAGTG GTCACTGTGA GCACTGCCAG
```

FIG. 7E

```
                                                         4320
    *          *          *          *          *          *          *          *
CTCAGCAAAT GTATCACCCA AAATCTGGGC AATGTGGGAA ATTGGCTTCA TGGCAGCTAT GGCTTTGCCA CTGATAGGAA

*          *          *          *          *          *          *          *
TGATTTCCAG AGATACTTAA TCCTCAATTC GGGACTCTTT GCTTCAGGAG TTTGGCTGGC CAGGAACATG AGTGACAGTG

4480
    *          *          *          *          *          *          *          *
ACCTCTTGGC ACTTCAGCTG GGGGTGTAGC CAAGCAGACA AATGGAATCT TGTGCTGAAC CCAAACCTTC TAGAAACAGA

4560
    *          *          *          *          *          *          *          *
GCCTGTGAGC ATCACAAGAT ATGCCCTGAT GGAAGCTGAA GTTTAATTCA GCTGAGCGCT TGCCCCTTTC CAACCTGGTT

4640
    *          *          *          *          *          *          *          *
TCTTTTTGTT CCTTGAGTCC AGTCAGAATG CCATTCCCTG GCCAGCAGCC AGCCTTTAGT GACTGTCTCT GTTCTGCAAA

4720
    *          *          *          *          *          *          *          *
GCTCTGTATA TAGTTACTGA GTTTCTGCAG GGGGTGATCT TTGCTCTTGT CCTAAGAAAT AACTACAGTG TTTTAAGAAA

4800
    *          *          *          *          *          *          *          *
TATTTGAGGC CGGGTGCAGT GGTTCACACC TGTAATCCAG CACTTTGGGA GGCCAAGGCA GGTGGATCAT GAGGTCAAGA

4880
    *          *          *          *          *          *          *          *
GTTTGAGACC ATCATGGCCA ACATGGTGAA ACCCCATCTC TACTAAAAAT ACAAAAATTA GCTGGGTGTG GTGGCGGGCA

4960
    *          *          *          *          *          *          *          *
CCTGTAGTCC CAGCTACTCG GGAGGCTGAG GCAGGAGAAT CGCTTGAGCC TGGGAGGCGG AGGTTGCACT GAGCCGATAT
```

FIG. 7F

```
                                                          5040
     *          *          *          *          *        *          *          *
CACGCCACTG CACTCCAGCC TGGCGACAGA GCGAGACTCC ATCTCAAAAA AAAGAAAAAA TAAATAGTTG AAATAAAGAC

5120
     *          *          *          *          *        *          *          *
TGCACATAAA GACAAAAAAA AAGTTTATAA AGTTAAAAAA TAAAATAAAA AACAGGCTCC AGGCTGGATT GGGCCCAGAG

5200
     *          *          *          *          *        *          *          *
GCTGTAGGAC ACAGACCCCC AGCCAATGAC TTCATAAATC CGGATGTTAA TCAGCCTCAC CTGGGAATTT GGGGAGGGGA

5280
     *          *          *          *          *        *          *          *
CTCATTTTAA AACAGTTTCC TGGATTCTAA CCCAACCCAG AAAATCAGAC TCTTTGAGCT AAATTCTTAA GCTCCCTGGT

5360
     *          *          *          *          *        *          *          *
GATGATGATG GAACCAGTTT ATGGCTGACC CCAGAGTACC GTCTGAAAGA CGTGCCACAT CCCTCTCTCT CCAGCCTCCC

*          *
CTTCTCCTCC ATTCCCCAGG GAGAATTC
```

FIG. 7G

```
                                                              Δ1
MASGQGPGPPRQECGEPALPSASEEQVAQDTEEVFRSYVFYRHQQEQEAEGVAAPADPEMVT
                                                              ⊢→

Δ2                          Δ3
LPLQPSSTMGQVGRQLAIIGDDINRRYDSEFQTMLQHLQPTAENAYEYFTKIATSLFESGNWGR
    ⊢→                          ⊢→

VVALLGFGYRLALHVYQHGLTGFLGQVTRFVVDFMLHHCIARWIAQRGGWVAALNLGNGPILN

VLVVLGVVLLGQFVVRRFFKS
```

FIG. 11

METHODS AND COMPOSITIONS FOR DETECTING CDN APOPTOSIS-MODULATING PROTEINS

This application is a divisional of U.S. patent application Ser. No. 08/320,157, filed Oct. 7, 1994, now abandoned, which is a continuation-in-part of U.S. patent application Ser. No. 08/160,067, filed Nov. 30, 1993, now abandoned. The entire disclosure of the prior application is incorporated herein by reference.

FIELD OF THE INVENTION

This invention relates to novel proteins with apoptosis-modulating activity, recombinant DNA encoding is the proteins, compositions containing the proteins and methods of use thereof.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death may be initiated by a wide variety of signals, including hormones, serum growth factor deprivation, chemotherapeutic agents, ionizing radiation and infection by human immunodeficiency virus (HIV). Wyllie (1980) Nature, 284:555–556; Kanter et al. (1984) Biochem. Biophys. Res. Commun. 118:392–399; Duke and Cohen (1986) Lymphokine Res. 5:289–299; Tomei et al. (1988) Biochem. Biophys. Res. Commun. 155:324–331; Kruman et al. (1991) J. Cell. Physiol. 148:267–273; Ameisen and Capron (1991) Immunology Today 12:102; and Sheppard and Ascher (1992) J. AIDS 5:143. Agents that modulate the biological control of apoptosis thus have therapeutic utility in a wide variety of conditions.

Apoptotic cell death is characterized by cellular shrinkage, chromatin condensation, cytoplasmic blebbing, increased membrane permeability and interchromosomal DNA cleavage. Kerr et al. (1992) FASEB J. 6:2450; and Cohen and Duke (1992) Ann. Rev. Immunol. 10:267. The blebs, small, membrane-encapsulated spheres that pinch off of the surface of apoptotic cells, may continue to produce superoxide radicals which damage surrounding cell tissue and may be involved in inflammatory processes.

Bcl-2 was discovered at the common chromosomal translocation site t(14:18) in follicular lymphomas and results in aberrant over-expression of bcl-2. Tsujimoto et al. (1984) Science 226:1097–1099; and Cleary et al. (1986) Cell 47:19–28. The normal function of bcl-2 is the prevention of apoptosis; unregulated expression of bcl-2 in B cells is thought to lead to increased numbers of proliferating B cells which may be a critical factor in the development of lymphoma. McDonnell and Korsmeyer (1991) Nature 349:254–256; and, for review see, Edgington (1993) Bio/Tech. 11:787–792. Bcl-2 is also capable of blocking of γ irradiation-induced cell death. Sentman et al. (1991) Cell 67:879–888; and Strassen (1991) Cell 67:889–899. It is now known that bcl-2 inhibits most types of apoptotic cell death and is thought to function by regulating an antioxidant pathway at sites of free radical generation. Hockenbery et al. (1993) Cell 75:241–251.

While apoptosis is a normal cellular event, it can also be induced by pathological conditions and a variety of injuries. Apoptosis is involved in a wide variety of conditions including but not limited to, cardiovascular disease, cancer regression, immunoregulation, viral diseases, anemia, neurological disorders, gastrointestinal disorders, including but not limited to, diarrhea and dysentery, diabetes, hair loss, rejection of organ transplants, prostate hypertrophy, obesity, ocular disorders, stress and aging.

Bcl-2 belongs to a family of proteins some of which have been cloned and sequenced. Williams and Smith (1993) Cell 74:777–779. All references cited herein, both supra and infra, are hereby incorporated by reference herein.

SUMMARY OF THE INVENTION

Substantially purified DNA encoding novel bcl-2 homologs, termed cdn-1, cdn-2 and cdn-3, as well as recombinant cells and transgenic animals expressing the cdn-1 and cdn-2 genes are provided. The substantially purified CDN-1 and CDN-2 proteins and compositions thereof are also provided. Diagnostic and therapeutic methods utilizing the DNA and proteins are also provided. Methods of screening for pharmaceutical agents that stimulate, as well as pharmaceutical agents that inhibit cdn-1 and cdn-2 activity levels are also provided.

BRIEF DESCRIPTION OF THE DRAWINGS

FIG. 1 depicts the PCR primers used to isolate the cdn-1 probes (SEQ ID NO:1 through SEQ ID NO:5, from top to bottom).

FIG. 3 depicts the nucleotide sequence (SEQ ID NO:6) and the predicted amino acid sequence (SEQ ID NO:7) of cdn-1.

FIG. 5 shows the sequence of the cdn-2 cDNA and flanking sequences (SEQ ID NO:8) and the corresponding predicted amino acid sequence (SEQ ID NO:9) of the cdn-2 protein.

FIG. 6 shows a comparison of N-terminal amino acid sequences of cdn-1 (SEQ ID NO:10), cdn-2 (SEQ ID NO:11) and known bcl-2 family members (SEQ ID NO:12 through SEQ ID NO:19, from bcl-2 through ced-9).

FIG. 7 shows the nucleotide sequence (SEQ ID NO:20) and the predicted amino acid sequence (SEQ ID NO:21) of cdn-3.

FIG. 11 depicts the cdn-1 (SEQ ID NO:7) derivative proteins Δ1 (positions 60–211 of SEQ ID NO:7), Δ2 (positions 71–211 of SEQ ID NO:7) and Δ3 (positions 96–211 of SEQ ID NO:7). The N-terminal residues are indicated by the arrows. The remainder of the derivative proteins is the same as full-length cdn-1.

DETAILED DESCRIPTION OF THE INVENTION

The present invention encompasses substantially purified nucleotide sequences encoding the novel bcl-2 homologs, cdn-1 and cdn-2; and the proteins encoded thereby; compositions comprising cdn-1 and cdn-2 genes and proteins and methods of use of thereof. Note that in copending U.S. patent application Ser. No. 08/160,067, cdn-1 was termed cdi-1; although the name has been changed, the nucleotide sequence remains identical. The invention further includes recombinant cells and transgenic animals expressing the cloned cdn-1 or cdn-2 genes. The nucleotide and predicted amino acid residue sequences of cdn-1 are shown in FIG. 3; and those of cdn-2 are shown in FIG. 5. It has now been found that the proteins encoded by the cdn genes are capable of modulating apoptosis. In a lymphoblastoid cell line, cdn-1 was shown to decrease Fas-mediated apoptosis. In a mouse progenitor B cell line, FL5.12, cdn-2 and a derivative of cdn-1 decrease IL-3-induced apoptosis whereas cdn-1 slightly increased apoptosis. Thus, depending on the cell type, the derivative of cdn and the method of induction of apoptosis, apoptosis can be modulated in a highly specific manner by controlling the concentration of cdns.

Figure 2:
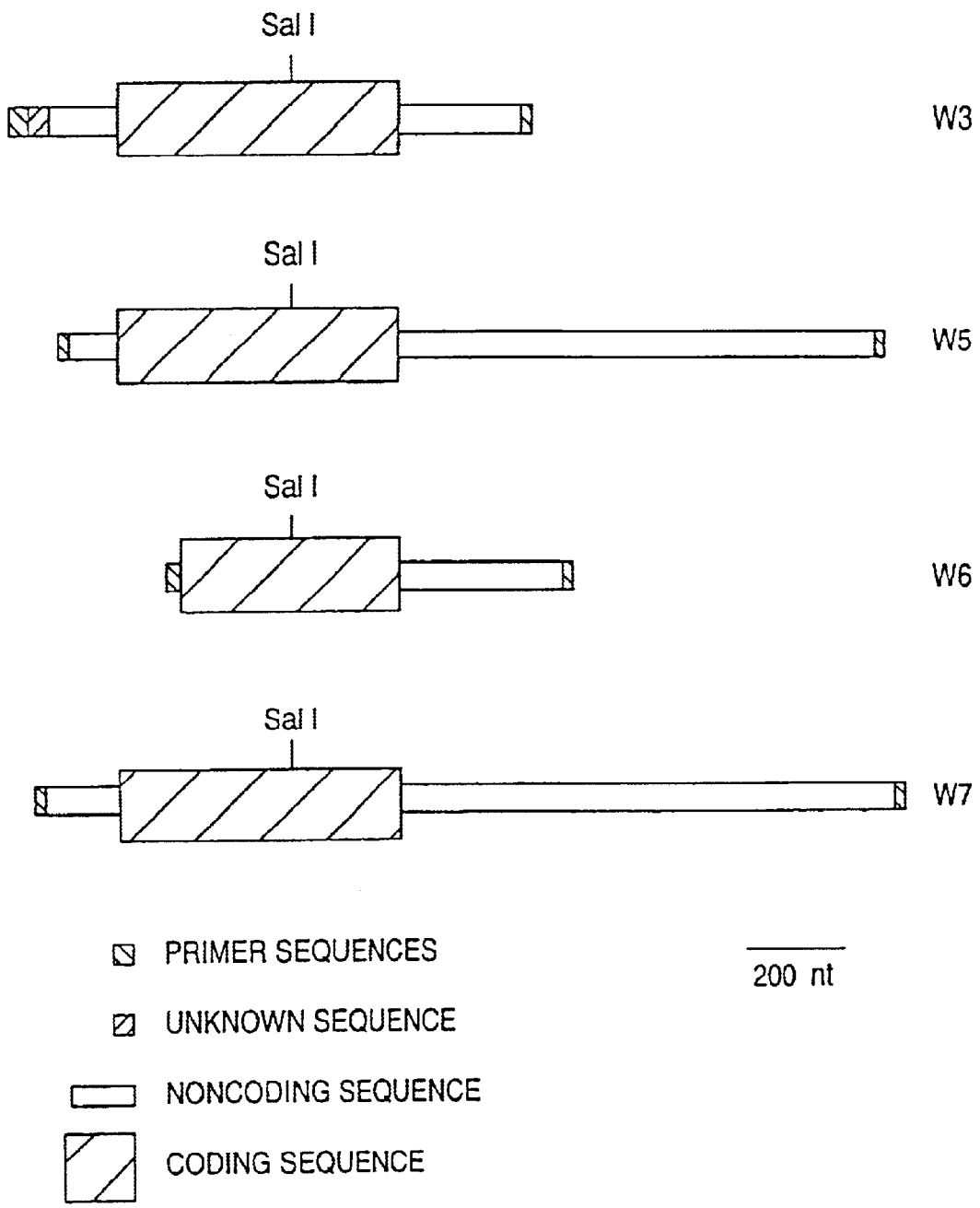
FIG. 2 depicts the cdn-1 clones obtained by the methods described in Example 1.

As used herein, "cdns" or "cdn" refers to the nucleic acid molecules described herein (cdn-1, cdn-2, cdn-3 and derivatives thereof), "the CDNs" or "CDN" refers to the proteins encoded thereby (CDN-1, CDN-2, CDN-3 and derivatives thereof). The present invention encompasses cdn-1 and cdn-2 nucleotide sequences. The cdn nucleotides include, but are not limited to, the cDNA, genome-derived DNA and synthetic or semi-synthetic DNA or RNA. The nucleotide sequence of the cdn-1 cDNA with the location of restriction endonuclease sites is shown in FIG. 2. As described in the examples herein, cdn-1 mRNA has been detected in a variety of human organs and tissues by Northern blot analysis. These organs include liver; heart; skeletal muscle; lung; kidney; and pancreas as shown in FIG. 3.

Similarly, cdn-2, cdn cDNA, genomic DNA and synthetic or semi-synthetic DNAs and RNAs are additional embodiments of the present invention. The nucleotide sequence of cdn-2 cDNA, along with the predicted amino acid sequence of cdn-2 protein and the locations of restriction endonuclease recognition sites, is given in FIG. 5. The examples presented herein indicate that cdn-1 is on human chromosome 6 and that cdn-2 is on human chromosome 20. There is also a member of the family cdn-3 which is on human chromosome 11. Fluorescence in situ hybridization (FISH) indicated an approximate location of cdn-1 to be at 6p21-23. Within this region resides the gene for spinocerebellar ataxia type 1. Interestingly, apoptosis has been proposed recently to be involved in the related genetic disorder ataxia telangiectasia. Taken together with the chromosomal localization and the expression of cdn-1 in brain tissue, this suggests the possibility that cdn-1/cdn-2 might represent the SCA1 gene locus. It is possible that cdn-2 and cdn-3 are pseudogenes. While these may not be expressed endogenously, they are capable of expression from a recombinant vector providing the appropriate promoter sequences. Thus, both cdn-2 and cdn-3 genes are encompassed by the present invention as are recombinant constructs thereof and proteins encoded thereby.

Figure 10:
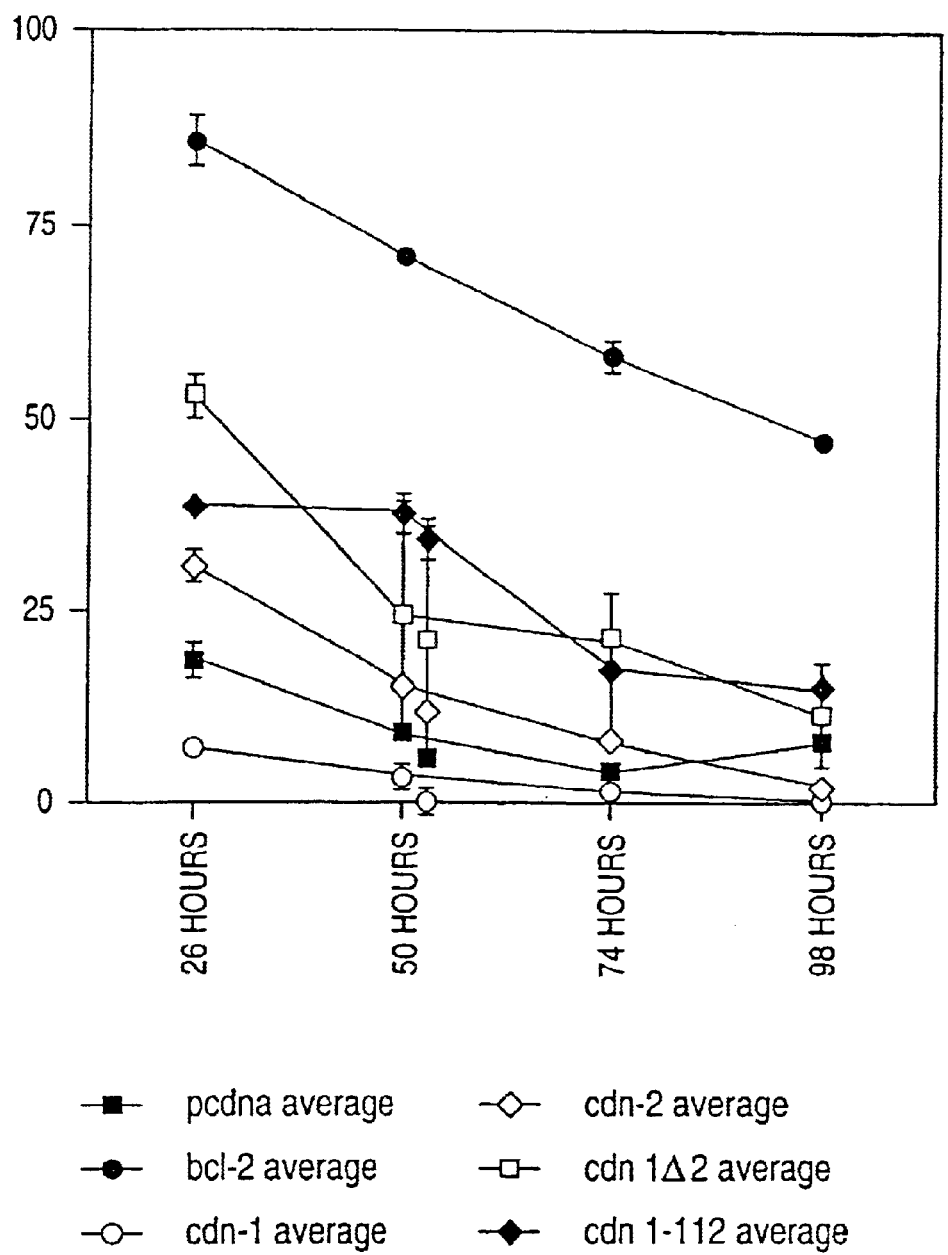
FIG. 10 shows modulation of apoptosis by cdn-1 and cdn-2 in FL5.12 cells.

Derivatives of the genes and proteins include any portion of the protein, or gene encoding the protein, which retains apoptosis modulating activity. FIG. 10 depicts three such derivatives of cdn-1 which have been shown to retain apoptosis-modulating activity. These derivatives, cdn1-Δ1, cdn1-Δ2 and cdn1-Δ3, are encompassed by the present invention.

The invention includes modifications to cdn DNA sequences such as deletions, substitutions and additions particularly in the non-coding regions of genomic DNA. Such changes are useful to facilitate cloning and modify gene expression.

Various substitutions can be made within the coding region that either do not alter the amino acid residues encoded or result in conservatively substituted amino acid residues. Nucleotide substitutions that do not alter the amino acid residues encoded are useful for optimizing gene expression in different systems. Suitable substitutions are known to those of skill in the art and are made, for instance, to reflect preferred codon usage in the particular expression systems.

The invention encompasses functionally equivalent variants and derivatives of cdns which may enhance, decrease or not significantly affect the properties of CDNs. For instance, changes in the DNA sequence that do not change the encoded amino acid sequence, as well as those that result in conservative substitutions of amino acid residues, one or a few amino acid deletions or additions, and substitution of amino acid residues by amino acid analogs are those which will not significantly affect its/properties.

Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Any conservative amino acid substitution which does not significantly affect the properties of CDNs is encompassed by the present invention.

Techniques for nucleic acid manipulation useful for the practice of the present invention are described in a variety of references, including but not limited to, *Molecular Cloning: A Laboratory Manual,* 2nd ed., Vol. 1–3, eds. Sambrook et al. Cold Spring Harbor Laboratory Press (1989); and *Current Protocols in Molecular Biology,* eds. Ausubel et al., Greene Publishing and Wiley-Interscience: New York (1987) and periodic updates.

The invention further embodies a variety of DNA vectors having cloned therein the cdn nucleotide sequences encoding CDN proteins. Suitable vectors include any known in the art including, but not limited to, those for use in bacterial, mammalian, yeast and insect expression systems. Specific vectors are known in the art and need not be describe in detail herein.

The vectors may also provide inducible promoters for expression of the cdns. Inducible promoters are those which do not allow constitutive expression of the gene but rather, permit expression only under certain circumstances. Such promoters may be induced by a variety of stimuli including, but not limited to, exposure of a cell containing the vector to a ligand, metal ion, other chemical or change in temperature.

These promoters may also be cell-specific, that is, inducible only in a particular cell type and often only during a specific period of time. The promoter may further be cell cycle specific, that is, induced or inducible only during a particular stage in the cell cycle. The promoter may be both cell type specific and cell cycle specific. Any inducible promoter known in the art is suitable for use in the present invention.

The invention further includes a variety of expression systems transfected with the vectors. Suitable expression systems include but are not limited to bacterial, mammalian, yeast and insect. Specific expression systems and the use thereof are known in the art and are not described in detail herein.

The invention encompasses ex vivo transfection with cdns, in which cells removed from animals including man are transfected with vectors encoding CDNs and reintroduced into animals. Suitable transfected cells include individual cells or cells contained within whole tissues. In addition, ex vivo transfection can include the transfection of cells derived from an animal other than the animal or human subject into which the cells are ultimately introduced. Such grafts include, but are not limited to, allografts, xenografts, and fetal tissue transplantation.

Essentially any cell or tissue type can be treated in this manner. Suitable cells include, but are not limited to, cardiomyocytes and lymphocytes. For instance, lymphocytes, removed, transfected with the recombinant DNA and reintroduced into an HIV-positive patient may increase the half-life of the reintroduced T cells.

As an example, in treatment of HIV-infected patients by the above-described method, the white blood cells are removed from the patient and sorted to yield the $CD4^+$ cells. The $CD4^+$ cells are then transfected with a vector encoding CDNs and reintroduced into the patient. Alternatively, the unsorted lymphocytes can be transfected with a recombinant vector having at least one cdn under the control of a cell-specific promoter such that only $CD4^+$ cells express the cdn genes. In this case, an ideal promoter would be the CD4 promoter; however, any suitable $CD4^+$ T cell-specific promoter can be used.

Further, the invention encompasses cells transfected in vivo by the vectors. Suitable methods of in vivo transfection are known in the art and include, but are not limited to, that described by Zhu et al. (1993) Science 261:209–211. In vivo transfection by cdns may be particularly useful as a prophylactic treatment for patients suffering from atherosclerosis. Elevated modulation of the levels of CDN could serve as a prophylaxis for the apoptosis-associated reperfusion damage that results from cerebral and myocardial infarctions. In these patients with a high risk of stroke and heart attack, the apoptosis and reperfusion damage associated with arterial obstruction could be prevented or at least mitigated.

Infarctions are caused by a sudden insufficiency of arterial or venous blood supply due to emboli, thrombi, or pressure that produces a macroscopic area of necrosis; the heart, brain, spleen, kidney, intestine, lung and testes are likely to be affected. Apoptosis occurs to tissues surrounding the infarct upon reperfusion of blood to the area; thus, modulation of CDN levels, achieved by a biological modifier-induced change in endogenous production or by in vivo transfection, could be effective at reducing the severity of damage caused by heart attacks and stroke.

Transgenic animals containing the recombinant DNA vectors are also encompassed by the invention. Methods of making transgenic animals are known in the art and need not be described in detail herein. For a review of methods used to make transgenic animals, see, e.g. PCT publication no. WO 93/04169. Preferably, such animals express recombinant cdns under control of a cell-specific and, even more preferably, a cell cycle specific promoter.

In another embodiment, diagnostic methods are provided to detect the expression of cdns either at the protein level or the mRNA level. Any antibody that specifically recognizes CDNs is suitable for use in CDN diagnostics. Abnormal levels of CDNs are likely to be found in the tissues of patients with diseases associated with inappropriate apoptosis; diagnostic methods are therefore useful for detecting and monitoring biological conditions associated with such apoptosis defects.

Detection methods are also useful for monitoring the success of CDN-related therapies.

Purification or isolation of CDNs expressed either by the recombinant DNA or from biological sources such as tissues can be accomplished by any method known in the art. Protein purification methods are known in the art. Generally, substantially purified proteins are those which are free of other, contaminating cellular substances, particularly proteins. Preferably, the purified CDNs are more than eighty percent pure and most preferably more than ninety-five percent pure. For clinical use as described below, the CDNs are preferably highly purified, at least about ninety-nine percent pure, and free of pyrogens and other contaminants.

Suitable methods of protein purification are known in the art and include, but are not limited to, affinity chromatography, immunoaffinity chromatography, size exclusion chromatography, HPLC and FPLC. Any purification scheme that does not result in substantial degradation of the protein is suitable for use in the present invention.

The invention also includes the substantially purified CDNs having the amino acid residue sequences depicted in FIGS. 3 and 5, respectively. The invention encompasses functionally equivalent variants of CDNs which do not significantly affect their properties and variants which retain the same overall amino acid sequence but which have enhanced or decreased activity. For instance, conservative substitutions of amino acid residues, one or a few amino acid deletions or additions, and substitution of amino acid residues by amino acid analogs are within the scope of the invention.

Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Any conservative amino acid substitution which does not significantly affect the properties of CDNs is encompassed by the present invention.

Suitable antibodies are generated by using the CDNs as an antigen or, preferably, peptides encompassing the CDN regions that lack substantial homology to the other gene products of the bcl family. Methods of detecting proteins using antibodies and of generating antibodies using proteins or synthetic peptides are known in the art and are not be described in detail herein.

The invention thus encompasses a method of detecting the presence of a CDN protein in a biological sample comprising the steps of: obtaining a cell sample; lysing or permeabilizing the cells to the antibodies; adding anti-CDN-specific antibodies to the cell sample; maintaining the cell sample under conditions that allow the antibodies to complex with the CDN; and detecting the antibody-CDN complexes formed. The cell sample can be comprised of T cells.

Methods of treatment with cdns also include modulating cellular expression of cdns by increasing or decreasing levels of cdn mRNA or protein. Suitable methods of increasing cellular expression of cdn include, but are not limited to, increasing endogenous expression and transfecting the cells with vectors encoding cdns. Cellular transfection is discussed above and is known in the art. Suitable indications for increasing endogenous levels of cdn include, but are-not limited to, malignancies and cardiac-specific over-expression. Cardiac specific over-expression is particularly suitable for use in indications including, but not limited to, patients susceptible to heart disease and in advance of cardiotoxic therapies including, but not limited to, chemotherapies such as adriamycin, so as to offer cardioprotection.

In addition, increasing endogenous expression of cdns can be accomplished by exposing the cells to biological modifiers that directly or indirectly increase levels of CDNs either by increasing expression or by decreasing degradation of cdn mRNA. Suitable biological modifiers include, but are not limited to, molecules and other cells. Suitable molecules include, but are not limited to, drugs, cytokines, small molecules, hormones, combinations of interleukins, lectins and other stimulating agents e.g. PMA, LPS, bispecific antibodies and other agents which modify cellular functions or protein expression. Cells are exposed to such biological modifiers at physiologically effective concentrations, and the expression of cdns is measured relative to a control not exposed to the biological modifiers. Those biological modifiers which increase expression of cdns relative to the control are selected for further study.

The invention further encompasses a method of decreasing endogenous levels of cdns. The methods of decreasing endogenous levels of cdns include, but are not limited to, antisense nucleotide therapy and down-regulation of expression by biological modifiers. Antisense therapy is known in the art and its application will be apparent to one of skill in the art.

Screening for therapeutically effective biological modifiers is done by exposing the cells to biological modifiers which may directly or indirectly decrease levels of CDNs either by decreasing expression or by increasing the half-life of cdn MRNA or CDNs. Suitable biological modifiers include, but are not limited to, molecules and other cells. Suitable molecules include, but are not limited to, drugs, cytokines, small molecules, hormones, combinations of interleukins, lectins and other stimulating agents e.g. PMA, LPS, bispecific antibodies and other agents which modify cellular functions or protein expression. Cells are grown under conditions known to elicit expression of at least one cdn (preferably cdn-1), exposed to such biological modifiers at physiologically effective concentrations, and the expression of cdns is measured relative to a control not exposed to biological modifiers. Those biological modifiers which decrease the expression of cdns relative to a control are selected for further study. Cell viability is also monitored to ensure that decreased cdn expression is not due to cell death.

In determining the ability of biological modifiers to modulate (increase or decrease) cdn expression, the levels of endogenous expression may be measured or the levels of recombinant fusion proteins under control of cdn-specific promoter sequences may be measured. The fusion proteins are encoded by reporter genes.

Reporter genes are known in the art and include, but are not limited to chloramphenicol acetyl transferase (CAT) and β-galactosidase. Expression of cdn-1 and -2 can be monitored as described above either by protein or mRNA levels. Expression of the reporter genes can be monitored by enzymatic assays, or antibody-based assays, like ELISAs and RIAs, also known in the art. Potential pharmaceutical agents can be any therapeutic agent or chemical known to the art, or any uncharacterized compounds derived from natural sources such as fungal broths and plant extracts. Preferably, suitable pharmaceutical agents are those lacking substantial cytotoxicity and carcinogenicity.

Suitable indications for modulating endogenous levels of cdns are any in which cdn-mediated apoptosis is involved. These include, but are not limited to, various types of malignancies and other disorders resulting in uncontrolled cell growth such as eczema, or deficiencies in normal programmed cell death such as malignancies, including, but not limited to, B cell lymphomas.

The invention also encompasses therapeutic methods and compositions involving treatment of patients with biological modifiers to increase or decrease expression of CDNs. Effective concentrations and dosage regimens may be empirically derived. Such derivations are within the skill of those in the art and depend on, for instance, age, weight and gender of the patient and severity of the disease. Alternatively, patients may be directly treated with either native or recombinant CDNs. The CDNs should be substantially pure and free of pyrogens. It is preferred that the recombinant CDNs be produced in a mammalian cell line so as to ensure proper glycosylation. CDNs may also be produced in an insect cell line and will be glycosylated.

For therapeutic compositions, a therapeutically effective amount of substantially pure CDN is suspended in a physiologically accepted buffer including, but not limited to, saline and phosphate buffered saline (PBS) and administered to the patient. Preferably administration is intravenous. Other methods of administration include but are not limited to, subcutaneous, intraperitoneal, gastrointestinal and directly to a specific organ, such as intracardiac, for instance, to treat cell death related to myocardial infarction.

Suitable buffers and methods of administration are known in the art. The effective concentration of a CDN will need to be determined empirically and will depend on the type and severity of the disease, disease progression and health of the patient. Such determinations are within the skill of one in the art.

Bcl-2 is thought to function in an antioxidant pathway. Veis et al. (1993) *Cell* 75:229–240. Therefore, therapy involving CDNs is suitable for use in conditions in which superoxide is involved. Administration of CDNs results in an increased extracellular concentration of CDNs, which is thought to provide a method of directly inhibiting superoxide accumulation that may be produced by the blebs associated with apoptosis. The therapeutic method thus includes, but is not limited to, inhibiting superoxide mediated cell injury.

Suitable indications for therapeutic use of CDNs are those involving free radical mediated cell death and include, but are not limited to, conditions previously thought to be treatable by superoxide dismutase. Such indications include but are not limited to HIV infection, autoimmune diseases, cardiomyopathies, neuronal disorders, hepatitis and other liver diseases, osteoporosis, and shock syndromes, including, but not limited to, septicemia.

Figure 8:
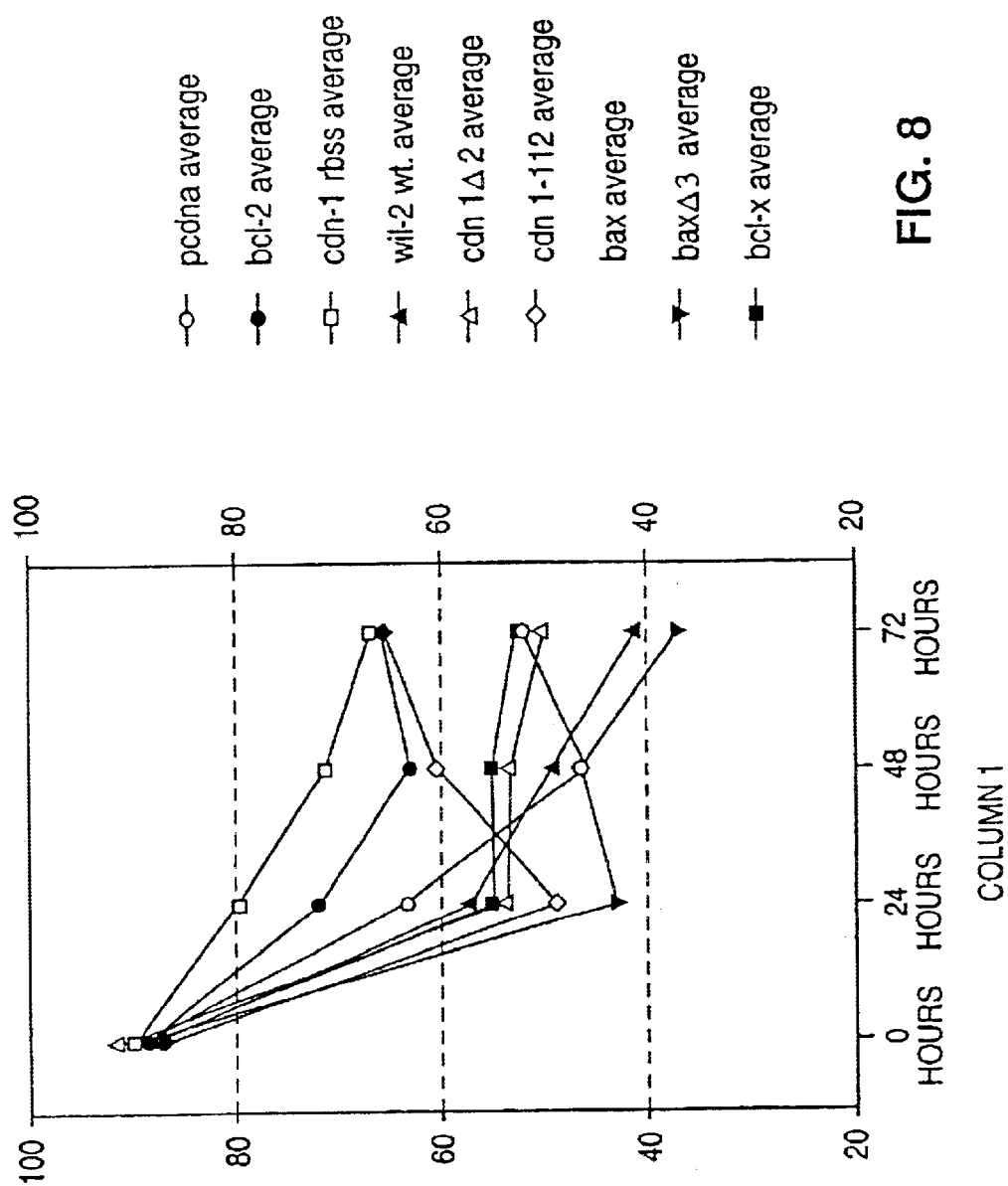
FIG. 8 shows the anti-apoptotic effects of cdn-1 and some of its derivatives in serum-deprivation induced apoptosis of WIL-2 cells.

Hybridization of cloned cdn DNA to messenger mRNA from various regions of the brain indicated high levels of expression of cdn-1 in each of the regions studied (FIG. 8). Therefore, neurological disorders are another area in which therapeutic applications of CDNs may be indicated.

The following examples are provided to illustrate but not limit the present invention. Unless otherwise specified, all cloning techniques were essentially as described by Sambrook et al. (1989) and all reagents were used according to the manufacturer's instructions.

EXAMPLE 1

Identification and Cloning of cdn-1 cDNA

An amino acid sequence comparison of the six known bcl-2 family members (FIG. 6) revealed two regions with considerable sequence identity, namely amino acids 144–150 and 191–199. In an attempt to identify new bcl-2 family members, degenerate PCR primers based on sequences in these regions were designed (FIG. 1) and PCR was performed using human heart CDNA and human B lymphoblastoid cell line (WIL-2) cDNA. PCR was performed using the Hot Start/Ampliwax technique (Perkin Elmer Cetus). The final concentration of the PCR primers and the template cDNA were 4 µM and 0.1–0.2 ng/ml, respectively. The conditions for cDNA synthesis were identical to those for first strand cDNA synthesis of the cDNA library as described below. PCR was performed in a Perkin Elmer Cetus DNA Thermal Cycler according to the method described by Kiefer et al. (1991) Biochem. Biophys. Res. Commun. 176:219–225, except that the annealing and extension temperatures during the first 10 cycles were 36° C. Following PCR, samples were treated with 5 units of DNA polymerase I, Klenow fragment for 30 min at 37° C. and then fractionated by electrophoresis on a 7% polyacrylamide, 1×TBE (Tris/borate/EDTA) gel. DNA migrating between 170–210 base pars was excised from the gel, passively eluted for 16 hours with gentle shaking in 10 mM Tris-HCI pH 7.5, 1 mM EDTA (TE), purified by passage over an Elutip-D column (Schleicher and Schuell), ligated to the pCR-Script vector (Stratagene) and transformed into *Escherichia coli* strain XL1-Blue MRF (Stratagene). Plasmid DNA from transformants (white colonies) containing both the heart and WIL-2 PCR products was isolated using the Magic Miniprep DNA Purification System (Promega), and the DNA inserts were sequenced by the dideoxy chain termination method according to Sanger et al. (1977) Proc. Natl. Acad. Sci. USA 74:5463–5467 (USB, Sequenase version 2.0). DNA sequence analysis of the eleven heart PCR products revealed two sequences identical to bcl-x (Boise et al. (1993) Cell 74:597–608) and ten other sequences unrelated to the bcl-2 family.

DNA sequence analyses of the eleven WIL-2 PCR products yielded one bcl-x sequence, five sequences identical to another bcl-2 family member, bax (Oldvai et al. (1993) Cell 74:609–619), four unrelated sequences and one novel bcl-2 related sequence, termed cdn-1. The unique cdn-1 amino acid sequence encoded by the PCR product is shown in FIG. 6 from amino acid 151–190 (top row).

To isolate the cdn-1 cDNA, a human heart cDNA library (Clontech) and a WIL-2 cDNA library, constructed as described by Zapf et al. (1990) J. Biol. Chem. 265:14892–14898 were screened using the cdn-1 PCR DNA insert as a probe. The DNA was $^{32}$P-labeled according to the method described by Feinberg and Vogelstein (1984) Anal. Biochem. 137:266–267 and used to screen 150,000 recombinant clones from both libraries according to the method described by Kiefer et al. (1991). Eight positive clones from the WIL-2 cDNA library and two positive clones from the heart cDNA library were identified. Four clones from the WIL-2 cDNA library and two from the heart cDNA library were further purified and plasmid DNA containing the cDNA inserts was excised from the λZAPII vector (Stratagene) (FIG. 2). The two longest clones, W7 (2.1 kb) and W5 (2.0 kb) were sequenced and shown to contain the cdn-1 probe sequence, thus confirming their authenticity. The heart cDNAs also encoded cdn-1.

The W7 DNA sequence along with the deduced amino acid residue sequence is shown in FIG. 2. The deduced amino acid sequence of cdn-1 was also aligned for maximum sequence identity with the other bcl-2 family members and is shown in FIG. 6. As can be seen, there is considerable sequence identity between cdn-1 and other family members between amino acids 100 and 200. Beyond this central region, sequence conservation falls off sharply. Like bcl-2, cdn-1 appears to be an intracellular protein in that it does not contain a either a hydrophobic signal peptide or N-linked glycosylation sites. Cdn-1 does contain a hydrophobic C-terminus that is also observed with all bcl-2 family members except LMW5-HL, suggesting its site of anti-apoptotic activity, like that of bcl-2, is localized to a membrane bound organelle such as the mitochondrial membrane, the endoplasmic reticulum or the nuclear membrane. Hockenbery et al. (1990); Chen-Levy et al. (1989) Mol. Cell. Biol. 9:701–710; Jacobsen et al. (1993) Nature 361:365–369; and Monighan et al. (1992) J. Histochem. Cytochem. 40:1819–1825.

EXAMPLE 2

Northern Blot Analysis of cDNA Clones

Northern blot analysis was performed according to the method described by Lehrach et al. (1977) Biochem. 16:4743–4651 and Thomas (1980) Proc. Natl. Acad. Sci. USA 77:5201–5205. In addition, a human multiple tissue Northern blot was purchased from Clontech. The coding regions of bcl-2 and cdn-1 cDNAs were labeled by the random priming method described by Feinberg and Vogelstein (1984) Anal. Biochem. 137:266–267. Hybridization and washing conditions were performed according to the methods described by Kiefer et al. (1991).

Figure 4:
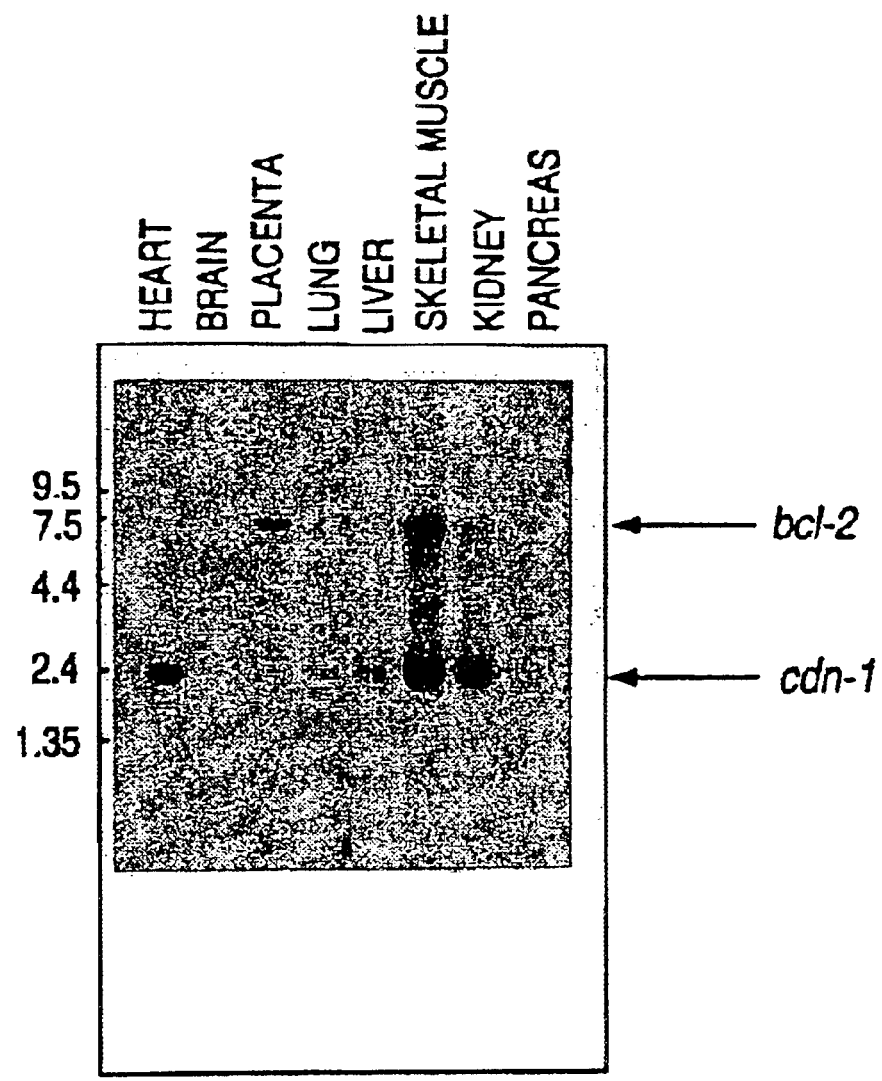
FIG. 4 depicts the results of a Northern blot analysis of multiple tissues with probes specific for both bcl-2 and cdn-1.

The results, presented in FIG. 4 indicate that cdn-1 is expressed in all organs tested (heart, brain, placenta, lung, liver, skeletal muscle, kidney and pancreas) whereas bcl-2 is not expressed or expressed at only low levels in heart, brain, lung, and liver. Thus, cdn-1 appears to be more widely expressed throughout human organs than bcl-2 and may be more important in regulating apoptosis in these tissues.

EXAMPLE 3

Expression of Recombinant cdn-1

In order to express recombinant cdn-1 in the baculovirus system, the cdn-1 cDNA generated in Example 1 was used to generate a novel cdn-1 vector, by a PCR methodology as described in Example 1, using primers from the 3' and 5' flanking regions of the gene which contain restriction sites to facilitate cloning. The plasmids were sequenced by the dideoxy terminator method (Sanger et al., 1977) using sequencing kits (USB, Sequenase version 2.0) and internal primers. This was to confirm that no mutations resulted from PCR.

A clone was used to generate recombinant viruses by in vivo homologous recombination between the overlapping sequences of the plasmid and AcNPV wild type baculovirus. After 48 hours post-transfection in insect *Spodoptera frugiperda* clone 9 (SF9) cells, the recombinant viruses were collected, identified by PCR and further purified. Standard procedures for selection, screening and propagation of recombinant baculovirus were performed (Invitrogen). The molecular mass, on sodium dodecyl sulfate-polyacrylamide gel electrophoresis (SDS-PAGE), of the protein produced in the baculovirus system was compared with the predicted molecular mass of cdn-1 according to the amino-acid sequence.

In addition, similar clones can be expressed preferably in a yeast intracellular expression system by any method known in the art, including the method described by Barr et al. (1992) Transcenesis ed. JAH Murray, (Wiley and Sons) pp. 55–79.

EXAMPLE 4

Expression of cdn-1 in Mammalian Systems

The cdn-1 coding sequence was excised from a plasmid generated in Example 1, and introduced into plasmids pCEP7, pREP7 and pcDNA3 (Invitrogen) at compatible restriction enzyme sites. pCEP7 was generated by removing the RSV 3'-LTR of pREP7 with XbaI/Asp718, and substituting the CMV promoter from pCEP4 (Invitrogen). 25 μg of each cdn-1-containing plasmid was electroporated into the B lymphoblastoid cell line WIL-2, and stable hygromycin resistant transformants or G418 resistant transformants (pcDNA3 constructs, FIG. 8) expressing cdn-1 were selected.

The coding region of cdns can also be ligated into expression vectors capable of stably integrating into other cell types including, but not limited to, cardiomyocytes, neural cell lines such as GTI-7, and TNF cell line HT29, so as to provide a variety of assay systems to monitor the regulation of apoptosis by cdn-1.

EXAMPLE 5

Effect of the Anti-Apoptotic Activity of cdn-1 and its Derivatives in the Wild Type B Lymphoblastoid Cell Line WIL2-729 HF2 and the Transformed Cell Expressing Excess cdn-1

$2 \times 10^5$ WIL-2, and WIL-2 cells transformed with a vector encoding cdn-1 as described in Example 4 are grown in RPMI supplemented with 10% fetal bovine serum (FBS) for the anti-fas experiment or 0.1% FBS for serum deprivation experiments. In the case of the anti-fas experiment, after washing with fresh medium, the cells were suspended in RPMI supplemented with 10% FBS, exposed to anti-fas antibodies and the kinetics of cell death in response to an apoptosis inducing agent were analyzed by flow cytometry with FACScan. In the case of the serum deprivation experiment, the WIL-2 cells were resuspended in RPMI supplemented with 0.1% FBS and apoptosis was monitored according to the method described by Henderson et al. (1993) Proc. Natl. Acad. Sci. USA 90:8479–8483. Other methods of inducing apoptosis include, but are not limited to, oxygen deprivation in primary cardiac myocytes, NGF withdrawal, glutathione depletion in the neural cell line GTI-7 or TNF addition to the HT29 cell line. Apoptosis was assessed by measuring cell shrinkage and permeability to propidium iodide (PI) during their death. In addition, any other method of assessing apoptotic cell death may be used.

Figure 9:
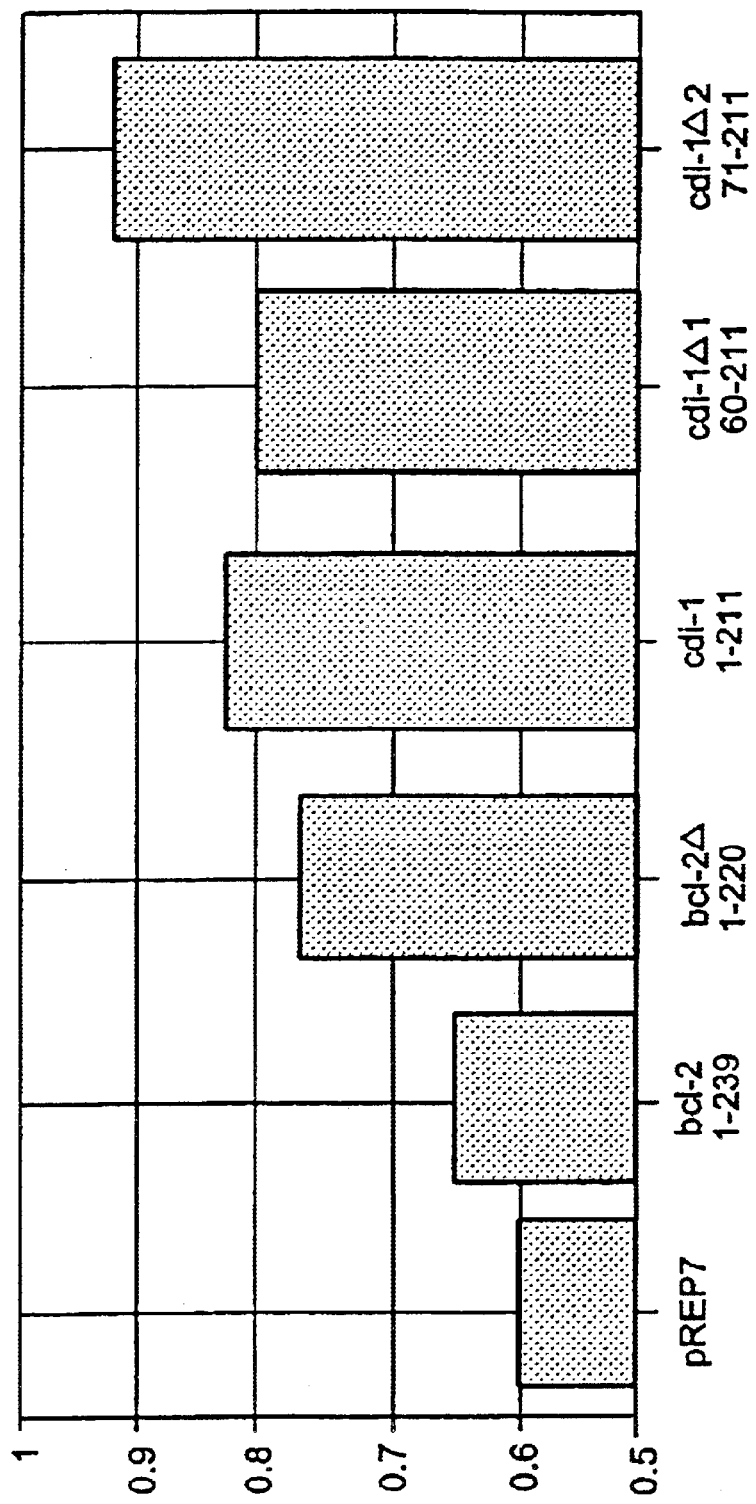
FIG. 9 shows anti-apoptotic effects of cdn-1 and some of its derivatives in FAS-induced apoptosis of WIL-2 cells.

FIG. 8 shows the anti-apoptotic response of various WIL-2 transformants to anti-Fas treatment. FIG. 9 shows the anti-apoptotic response of various WIL-2 transformants to serum deprivation. In FIG. 8, duplicate wells containing $3 \times 10^5$ cells were incubated with 50 ng/ml of the cytocidal anti-Fas antibody for 24 hours. Cell death was then analyzed by flow cytometry with FACScan. The proteins expressed from each construct are shown beneath the columns. Since many of the constructs are truncation or deletion variants, the exact amino acids expressed are also indicated. As can be seen, all of the transformants had some protective effect when compared to the control transformant containing the pREP7 vector alone. The most apoptosis-resistant transformant was the cdn-1Δ2 expressing cell line, in which over 90% of the cells survived anti-fas treatment. Significant protection was also observed in transformants expressing full length cdn-1 (1–211) and cdn-1Δ1, followed by bcl-2Δ and bcl-2 expressing cell lines.

Cdn-1Δ1 and cdn-1Δ2 are lacking the N-terminal 59 and 70 amino acids of the full length cdn-1 molecule, respectively. The observation that cdn-1Δ2 is more effective at blocking apoptosis than full length cdn-1 suggests that smaller, truncated cdn-1 molecules may be potent therapeutics.

EXAMPLE 6

Determination of other cdn Genes and Cloning of the cdn-2 Gene

Southern blot analyses of human genome DNA and a panel of human/rodent somatic cell DNAs indicated that there were at least 3 cdn related genes and that they resided in chromosomes 6, 11 and 20. PCR/sequence analysis of the three hybrid DNAs showed that cdn-1 was on chromosome 6 and that two closely related sequences were on chromosome 20 (designated cdn-2) and chromosome 11 (designated cdn-3). We have cloned the cdn-2 and cdn-3 genes and sequenced them. Interestingly, both cdn-2 and cdn-3 do not contain introns and have all of the features of processed genes that have returned to the genome. cdn-3 has a nucleotide deletion, causing a frame shift and early termination and thus is probably a pseudogene. Both, however, have promoter elements upstream of the repeats CCAAT, TATAAA boxes but are probably not transcribed. (Northern blot analysis with cdn-2 and cdn-3 specified probes.)

900,000 clones from a human placenta genomic library in the cosmid vector pWE15 (Stratagene, La Jolla, Calif.) were screened with a 950 bp BglII- HindIII cDNA probe containing the entire coding region of Cdn-1. The probe was $^{32}$P-labeled according to the method of Feinberg and Vogelstein (1984) Anal. Biochem. 137:266–267. The library was processed and screened under high stringency hybridization and washing conditions as described by Sambrook et al. (1989) Molecular Cloning, 2nd edition, Cold Spring Harbor Laboratory Press. Ten double positive clones were further purified by replating and screening as above. Plasmid DNA was purified using the Wizard Maxiprep DNA Purification System as described by the supplier (Promega Corp., Madison, Wis.) and analyzed by EcoRI restriction enzyme mapping and Southern blotting. The probe used for Southern blotting and hybridization conditions was the same as above.

The cosmid clones fell into two groups as judged by EcoRI restriction analysis and Southern blotting. Cosmid clones (cos) 1–4 and 7 displayed one distinct pattern of EcoRI generated DNA fragments and contained a single 6.5 kb hybridizing EcoRI DNA fragment. Cos2 and Cos9 fell into the second group that was characterized by a 5.5 kb hybridizing EcoRI DNA fragment. The 6.5 kb DNA fragment from cos2 and the 5.5 kb DNA fragment from cos9 were subcloned into pBluescript SK (Stratagene, La Jolla, Calif.) using standard molecular biological techniques (Sambrook et al. as above). Plasmid DNA was isolated and the DNA inserts from two subclones, A4 (from cos2) and C5 (from cos9) were mapped with BamHI, HindIII and EcoRI and analyzed by Southern blotting as described above. Smaller restriction fragments from both clones were subcloned into M13 sequencing vectors and the DNA sequence was determined.

The sequence of A4 contains an open reading frame that displays 97% amino acid sequence identity with cdn-1. (FIG. 5) The high degree of sequence identity of this gene with cdn-1 indicates that it is a new cdn-1 related gene and therefore will be called cdn-2. A sequence comparison of the encoded cdn-2 protein and the other members of the bcl-2 family is shown in FIG. 5. Cdn-2 contains the conserved regions, BH1 and BH2, that are hallmarks of the bcl-2 family, and displays a lower overall sequence identity (~20–30%) to other members, which is also characteristic of the bcl-2 family. cdn-3 has a frame shift and therefore does not contain the structural features of cdn-1, cdn-2 or other bcl-2 family members.

EXAMPLE 7

Chromosomal Localization of the cdn-1 and cdn-2 Genes

Southern blot analysis of a panel of human/rodent somatic cell hybrid DNAs (Panel #2 DNA from the NIGMS, Camden, N.J.) and fluorescent in situ hybridization (FISH) of metaphase chromosomes were used to map the cdn genes to human chromosomes. For Southern blotting, 5 μg of hybrid panel DNA was digested with EcoRI or BamHI/HindIII, fractionated on 0.8% or 1% agarose gels, transferred to nitrocellulose and hybridized with the cdn-1 probe. Hybridization and washing conditions were as described above. For FISH, the cdn-2 subclone, A4, was biotinylated using the Bionick Labeling System (Gibco BRL, Gaithersburg, Md.) and hybridized to metaphase chromosomes from normal human fibroblasts according to the method described by Viegas-Pequignot in In Situ Hybridization, A Practical Approach, 1992, ed. D. G. Wilkinson, pp. 137–158, IRL Press, Oxford. Probe detection using FITC-conjugated avidin and biotinylated goat anti-avidin was according to the method described by Pinkel et al. (1988) *Proc. Natl. Acad. Sci. USA* 85:9138–9142.

Southern blot analysis showed three hybridizing EcoRI bands in the human DNA control that were approximately 12 kb, 11 kb and 5.5 kb in length. Analysis of the somatic cell hybrid DNA indicated that the 12 kb band was in two different samples, NA10629, which contained only human chromosome 6, and NA07299, which contained both human chromosomes 1 and X and, importantly, a portion of chromosome 6 telomeric to p21. The 11 kb band was in NA13140, which contains human chromosome 20. The 5.5 kb hybridizing band was found only in sample NA10927A, which contained human chromosome 11. PCR/DNA sequencing analysis of these hybrid DNA samples using primers for cdn-1 or cdn-2, showed cdn-1 sequences in NA10629 (the chromosome 6-containing hybrid DNA) and NA07299 (the chromosome 1, X and 6pter >p21-containing hybrid DNA), indicating that the cdn-1 gene resides on chromosome 6, telomeric to p21. cdn-2 sequences were found in NA13140, indicating the cdn-2 gene resides on chromosome 20, and cdn-3 sequences were found in NA10927A, indicating the cdn-3 gene resides on chromosome 11.

EXAMPLE 8

Modulation of Apoptosis by cdn-1 and cdA-2 in FL5.12 Cells

FL5.12 is an IL-3-dependent lymphoid progenitor cell line (McKearn et al. (1985) *Proc. Natl. Acad. Sci USA* 82:7414–7418) that has been shown to undergo apoptosis following withdrawal of IL-3 but is protected from cell death by overexpression of bcl-2. Nunez et al. (1990) *J. Immunol.* 144:3602–3610; and Hockenbery et al. (1990) *Nature* 348:334–336. To assess the ability of cdn-1 and cdn-2 to modulate apoptosis, cDNAs encoding cdn-1, cdn-2, two truncated forms of cdn-1 (described below) and bcl-2 were ligated into the mammalian expression vector, pcDNA3 (Invitrogen, San Diego, Calif.) and stably introduced into the mouse progenitor B lymphocyte cell line FL5.12 by electroporation and selection in media containing the antibiotic G418. Assays were then performed on bulk transformants as described below.

The effects of the overexpressed genes on FL5.12 cell viability were examined at various times following withdrawal of IL-3 and are shown in FIG. 10. Cell viability was assessed by propidium iodide (PI) exclusion on a flow cytometer (Becton Dickinson FACScan). Bcl-2 expression protected the cells significantly from cell death while cdn-1 appeared to enhance cell death when compared to the vector control. Cdn-2 expression conferred a low level of protection from cell death at earlier times but was insignificant at later time points. Interestingly, cdn-1Δ2 gave a moderate level of protection against cell death. Cdn-1–112, a molecule that contains the N-terminal 112 amino acids of cdn-1, also appeared to partially protect the FL5.12 cells although at lower levels than Bcl-2.

As shown in Example 7, expression of cdn-1 and cdn-1Δ2 in WIL2 cells resulted in increased cell survival in response to anti-Fas-mediated apoptosis and serum withdrawal. Taken together, these data suggest that the various cdn molecules are capable of modulating apoptosis in a positive or negative manner, depending on the cell type and apoptotic stimuli. Thus, they are effective in preventing cell death such as in the post-ischemic reperfusion tissue damage in the heart or in inducing cell death in cells that have escaped apoptotic control, as is the case in various cancers.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

We claim:

1. A composition comprising a monoclonal or polyclonal antibody which specifically binds to SEQ ID NO: 7, CDN-1.

2. The composition of claim 1, wherein the antibody is a monoclonal antibody.

3. A method of detecting the presence of CDN-1, SEQ ID NO: 7 in a biological sample comprising the steps of:
   a) obtaining a cell sample;
   b) lysing or permeabilizing the cells to antibodies;
   c) adding the antibody of claim 1 to the cell sample;
   d) maintaining the cell sample under conditions that allow the antibody to complex with CDN-1, SEQ ID NO: 7; and
   e) detecting antibody-CDN-1, SEQ ID NO: 7, complexes formed, thus detecting CDN protein.

4. The method according to claim 3, wherein the cell sample comprises T cells.

* * * * *